United States Patent [19]

Hoshino et al.

[11] Patent Number: 5,753,707
[45] Date of Patent: May 19, 1998

[54] AMIDE DERIVATIVES AND THEIR USE IN COSMETIC COMPOSITION

[75] Inventors: Masahide Hoshino; Hiroshi Kusuoku; Tadashi Hase; Atsuko Otsuka; Ichiro Tokimitsu; Akira Yamamuro; Yoshiya Sugai; Koji Yoshino; Youichi Arai; Shinichi Meguro, all of Ichikai-machi, Japan

[73] Assignee: Kao Corporation, Tokyo, Japan

[21] Appl. No.: 708,974

[22] Filed: Sep. 6, 1996

[30] Foreign Application Priority Data

Sep. 7, 1995 [JP] Japan .................. 7-229875
Oct. 5, 1995 [JP] Japan .................. 7-258511
Feb. 6, 1996 [JP] Japan .................. 8-019762

[51] Int. Cl.⁶ .......... A61K 31/16; A61K 31/335; A61K 6/00; C07C 233/00
[52] U.S. Cl. .......... 514/616; 514/847; 514/463; 514/231.2; 564/160; 564/159; 564/152; 424/401; 560/250; 554/57; 554/61; 554/66; 549/452; 544/175
[58] Field of Search .................. 564/160, 159, 564/152, 199; 549/452, 450; 544/175; 424/401; 514/847, 616, 463, 231.2; 554/57, 63

[56] References Cited

U.S. PATENT DOCUMENTS

| | | | |
|---|---|---|---|
| 4,985,547 | 1/1991 | Yano et al. | 536/4.1 |
| 5,175,321 | 12/1992 | Oshashi et al. | 554/63 |
| 5,206,020 | 4/1993 | Critchley et al. | 424/401 |
| 5,208,355 | 5/1993 | Scott | 554/37 |
| 5,446,027 | 8/1995 | Fujimori et al. | 514/25 |

FOREIGN PATENT DOCUMENTS 4-225907   8/1992   Japan .
4-342553  11/1992   Japan .
7-70030    3/1995   Japan .

*Primary Examiner*—Richard L. Raymond
*Assistant Examiner*—Deborah Lambkin
*Attorney, Agent, or Firm*—Oblon, Spivak, McClelland, Maier & Neustadt, P.C.

[57] ABSTRACT

An amide derivative represented by the following formula (1):

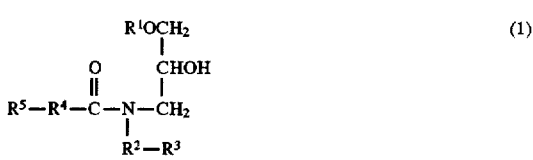

wherein $R^1$ represents a $C_{1-40}$ hydrocarbon; $R^2$ represents a $C_{1-6}$ alkylene; $R^3$ represents H, OH or alkoxyl; $R^4$ represents a $C_{1-39}$ hydrocarbon; $R^5$ represents

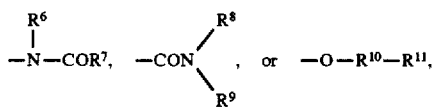

with the proviso that when $R^5$ represents

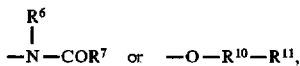

$R^3$ does not represent OH; and a composition of the amide derivative for topical application to human skin. The composition improves the barrier function of the stratum corneum, providing improvement and prevention of dermatitis, skin roughness, or similar disorders.

21 Claims, No Drawings

AMIDE DERIVATIVES AND THEIR USE IN COSMETIC COMPOSITION

BACKGROUND OF THE INVENTION

1. Field of the Invention

The present invention relates to novel amide derivatives which provide fundamental improvement of the barrier function of the stratum corneum, i.e., for maintenance of the normal barrier function, recovery from deterioration in the barrier function, and reinforcement thereof. The present invention further relates to compositions containing said derivative for topical application to human skin, hair, and nails. The novel amide derivatives have excellent stability in such compositions.

The stratum corneum is a thin layer of the epidermis, which forms the outermost layer of the body. The stratum corneum not only protects the body from various external stimuli, but also prevents loss of water or other components from the body. The protective function of the stratum corneum, i.e., the barrier function, is important for controlling homeostasis of the physiology of the epidermis.

Impairment of the barrier function due to internal or external causes, such as exposure to ultraviolet rays, results in epidermic disorders, e.g., dermatitis, rough skin, or acceleration of aging. Maintenance and reinforcement of the barrier function of the stratum corneum is extremely important for healthy daily life.

2. Description of the Related Art

To prevent or overcome the occurrence of such epidermic disorders, various compositions, containing components derived from natural products or chemically-synthesized components, have been developed for topical application to human skin. The primary object of such compositions for topical application to human skin is to provide a moisturizing effect, or to reinforce the barrier function of the skin by forming a film on the surface of the skin. These compositions only supplement the barrier function of the skin by temporarily forming a film on the surface of the skin. Thus, fundamental improvement (i.e., maintenance and reinforcement) of the barrier function cannot be expected from them.

The present inventor therefore proposed a composition for topical application to human skin (Japanese Patent Laid-Open No. 306952/1990) which is effective for the improvement of the epidermic barrier function, containing an amide derivative of formula (2):

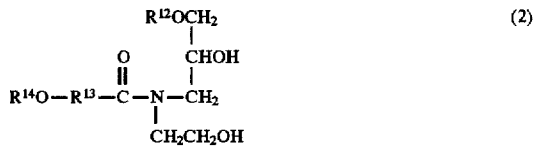

wherein $R^{12}$ represents a linear or branched, saturated or unsaturated $C_{10-40}$ hydrocarbon group, $R^{13}$ represents a linear or branched divalent $C_{3-39}$ hydrocarbon group, and $R^{14}$ represents a hydrogen atom, a linear or branched, saturated or unsaturated $C_{10-40}$ hydrocarbon group or an acyl group.

The present inventor also proposed a dermatological composition for external use (Japanese Patent Laid-Open No. 70030/1995) containing an amide derivative of formula (3):

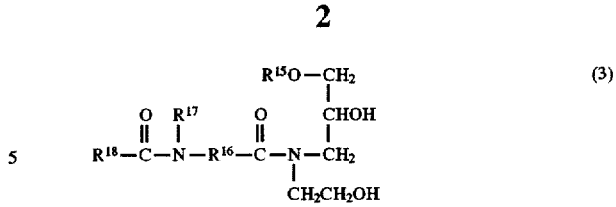

wherein $R^{15}$ represents a linear or branched $C_{10-40}$ hydrocarbon group, $R^{16}$ represents a linear or branched divalent $C_{1-39}$ hydrocarbon group, and $R^{17}$ represents a hydrogen atom or a $C_{1-6}$ hydrocarbon group. $R^{18}$ represents a hydrogen atom or a linear, branched or cyclic $C_{1-40}$ hydrocarbon group which may contain one or more oxygen atoms.

Scott et al proposed a cosmetic composition containing an amide derivative having a similar structure (Japanese Patents Laid-Open Nos. 225907/1992 and 342553/1992).

The above-described amide derivatives provide improvement of the epidermic barrier function by acting on the stratum corneum. However, they are not always satisfactory with respect to properties such as solubility in the base ingredients and stability of the compositions, which makes compositioning more difficult.

SUMMARY OF THE INVENTION

Accordingly, an object of the present invention is to provide a novel amide derivative.

Another object of the present invention is to provide a composition comprising said amide derivative, for topical application to human skin, which fundamentally improves (i.e., maintains and reinforces) the barrier function of the stratum corneum when applied to the skin, which can prevent and cure rough skin or dermatitis, and which also prevents epidermic aging.

Another object is to provide a composition for topical application to human skin comprising said amide derivative, which is improved in ease of preparation and in stability of the composition owing to a decrease in its melting point, lowering of crystallinity, and improvement of solubility in base ingredients.

DETAILED DESCRIPTION OF THE PREFERRED EMBODIMENTS

Having generally described this invention, a further understanding can be obtained by reference to certain specific examples which are provided herein for purposes of illustration only and are not intended to be limiting unless otherwise specified.

With the forgoing in view, the present inventors have carried out extensive research. It was found that the above-described objects can be accomplished by a novel amide derivative of formula (1), and a composition for topical application to human skin comprising said amide derivative.

The present invention provides an amide derivative of formula (1):

wherein $R^1$ represents a linear or branched $C_{1-40}$ hydrocarbon group;

$R^2$ represents a linear or branched $C_{16}$ alkylene group;

$R^3$ represents a hydrogen atom, a hydroxyl group or a linear or branched $C_{1-12}$ alkoxyl group which may be substituted by one or more hydroxyl groups;

$R^4$ represents a linear or branched divalent $C_{1-39}$ hydrocarbon group; and $R^5$ represents

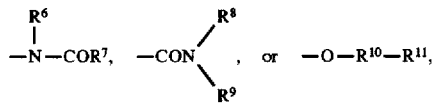

wherein:

$R^6$ represents a hydrogen atom or a $C_{16}$ hydrocarbon group.

$R^7$ represents a linear, branched, or cyclic $C_{1-40}$ hydrocarbon group which may contain one or more oxygen atoms.

$R^8$ and $R^9$ are the same or different and are individually a hydrogen atom or a linear, branched, or cyclic $C_{1-40}$ hydrocarbon group which may contain one or more oxygen atoms or are coupled together to form a divalent $C_{1-40}$ hydrocarbon group which may contain one or more oxygen atoms.

$R^{10}$ represents a carbonyl group, a methylene group, or a single bond, and $R^{11}$ represents a linear, branched, or cyclic $C_{1-40}$ hydrocarbon group which may contain one or more oxygen atoms or a hydrogen atom, with the proviso that when $R^{10}$ represents a single bond, $R^{11}$ represents a hydrogen atom, and with the proviso that when $R^5$ represents

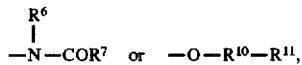

$R^3$ does not represent a hydroxyl group.

The present invention further provides a composition for topical application to human skin comprising said amide derivative.

The amide derivative according to the present invention provides fundamental improvement (i.e., maintenance and reinforcement) of the barrier function of the stratum corneum; and has good solubility and stability to the base ingredients, owing to a low melting point and low crystallinity, so that it can be incorporated stably and easily in the base. The composition for topical application to human skin comprising the amide derivative of the present invention therefore fundamentally improves the barrier function of the stratum corneum when applied to the skin, thereby improving and/or preventing dermatitis, rough skin and other disorders.

The amide derivative according to the present invention is represented by the above formula (1). In formula (1), a linear or branched $C_{1-40}$ hydrocarbon group represented by $R^1$ may be saturated or unsaturated.

Specific examples include, but are not limited to methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-heptacosyl, n-octacosyl, n-nonacosyl, n-triacontyl, n-hentriacontyl, n-dotriacontyl, n-tritriacontyl, n-tetratriacontyl, n-pentatriacontyl, n-hexatriacontyl, n-heptatriacontyl, n-octatriacontyl, n-nonatriacontyl, n-tetracontyl, ethenyl, propenyl, butenyl, pentenyl, hexenyl, octenyl, nonenyl, decenyl, undecenyl, tridecenyl, tetradecenyl, pentadecenyl, hexadecenyl, heptadecenyl, octadecenyl, nonadecenyl, icosenyl, henicosenyl, tocosenyl, tricosenyl, tetracosenyl, pentacosenyl, hexacosenyl, heptacosenyl, octacosenyl, nonacosenyl, triacontenyl, hentriacontenyl, dotriacontenyl, tritriacontenyl, tetratriacontenyl, pentatriacontenyl, hexatriacontenyl, heptatriacontenyl, octatriacontenyl, nonatriacontenyl, tetracontenyl, isostearyl, 2-ethylhexyl, 2-heptylundecyl, 9,12-octadecadienyl and the like.

Of these, preferred as $R^1$ are linear or branched $C_{1-26}$ hydrocarbon groups. More preferred are linear or branched, saturated $C_{4-26}$ hydrocarbon groups, with linear or branched-saturated $C_{4-22}$ hydrocarbon groups being still more preferred. Specific examples of the particularly preferred group include, but are not limited to butyl, hexyl, octyl, decyl, dodecyl, tetradecyl, hexadecyl, octadecyl, methyl-branched isostearyl group, docosanyl and the like. Among these examples, the methyl-branched isostearyl group is a mixture of the similar groups which are all categorized into said methyl-branched isostearyl group except that there is a variation in the positions of methyl constituents on their principal chain. The formation of such a mixture is ascribed to the use of isostearyl alcohol as a starting material, and said isostearyl alcohol can be obtained by reduction of the isostearic acid which is generated as a by-product in the process of producing dimer acid from beef tallow or soybean oil.

Examples of the linear or branched $C_{16}$ alkylene group represented by $R^2$ include, but are not limited to methylene, ethylene, trimethylene, tetramethylene, pentamethylene, hexamethylene, 1-methylethylene, 1-methyltrimethylene, 2-methyltrimethylene, 1,1-dimethylethylene, 1-ethylethylene, 1-methyltetramethylene, 2-ethyltrimethylene and the like. Of these, linear $C_{1-6}$ alkylene groups are preferred, with methylene, ethylene and trimethylene being particularly preferred.

$R^3$ represents a hydrogen atom, a hydroxyl group or a linear or branched $C_{1-12}$ alkoxyl group which may contain one or more hydroxyl groups. Specific examples of such an alkoxyl group include, but are not limited to methoxy, ethoxy, propoxy, butoxy, hexyloxy, octyloxy, decyloxy, 1-methylethoxy, 2-ethylhexyloxy, 2-hydroxyethyloxy, 2,3-dihydroxypropyloxy and the like. Of these, a hydrogen atom and hydroxyl, $C_{1-8}$ alkoxyl, 2-hydroxyethyloxy and 2,3-dihydroxypropyloxy groups are preferred as $R^3$, with a hydrogen atom and hydroxyl, methoxy, ethoxy, butoxy, 1-methylethoxy, 2-ethylhexyloxy, 2-hydroxyethyloxy and 2,3-dihydroxypropyloxy groups being particularly preferred.

Examples of the linear or branched divalent $C_{1-39}$ hydrocarbon group represented by $R^4$ include, but are not limited to methylene, dimethylene, trimethylene, tetramethylene, pentamethylene, hexamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, icosamethylene, henicosamethylene, docosamethylene, tricosamethylene, tetracosamethylene, pentacosamethylene, hexacosamethylene, heptacosamethylene, octacosamethylene, nonacosamethylene, heptadecane-1,11-diyl, 8-heptadecene-1,11-diyl and the like groups. Of these, preferred as $R^4$ are linear, saturated, divalent, hydrocarbon groups, with those having 5–31 carbon atoms being particularly preferred. Specific examples of the particularly preferred groups include nonamethylene, decamethylene, undecamethylene, tetradecamethylene, pentadecamethylene and hentriacontamethylene groups.

R$^5$ represents

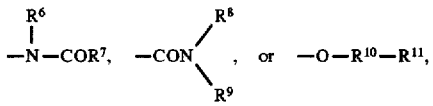

with the proviso that when R$^5$ is

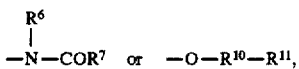

R$^3$ does not represent a hydroxyl group. In the above formula, R$^6$ represents a hydrogen atom or a C$_{1-6}$ hydrocarbon group. Specific examples of the hydrocarbon group include, but are not limited to methyl, ethyl, linear or branched propyl, butyl, pentyl, hexyl, vinyl, allyl, butenyl, pentenyl and hexynyl groups. As R$^6$, a hydrogen atom is preferred.

Examples of, as R$^7$, the linear, branched or cyclic C$_{1-40}$ hydrocarbon group which may contain one or more oxygen atom include, but are not limited to hydrocarbon groups containing one or more hydroxyl groups (—OH), ether bonds (—O—), carbonyl groups (—C(=O)—), carboxyl groups (—COOH), or carboxylate groups (—COO—). Specific examples of such a hydrocarbon group include, but are not limited to methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-heptacosyl, n-octacosyl, n-nonacosyl, n-triacontyl, n-hentriacontyl, n-dotriacontyl, n-tritriacontyl, n-tetratriacontyl, n-pentatriacontyl, n-hexatriacontyl, n-heptatriacontyl, n-octatriacontyl, n-nonatriacontyl, n-tetracontyl, 3-heptyl, 2,4,4-trimethylpentyl, 8-heptadecyl, isoheptadecyl, methyl-branched isoheptadecyl, 12-pentacosyl, cyclohexylethyl, 8-heptadecenyl, 8,11-heptadecadienyl, 8,11,14-heptadecatrienyl, cholesteryl, 8-hydroxyoctyl, 11-hydroxyundecyl, 14-hydroxytetradecyl, 15-hydroxypentadecyl, 11-hydroxyheptadecyl, 11-hydroxy-8-heptadecenyl, 8,9-dihydroxyheptadecyl, 11,12-dihydroxy-8-heptadecenyl, 11-methoxyheptadecyl, 11-ethoxyheptadecyl, 11-benzyloxyheptadecyl, 11-methoxy-8-heptadecenyl, 11-ethoxy-8-heptadecenyl, 11-benzyloxy-8-heptadecenyl, 9,10-(isopropylidenedioxy)decyl, 8,9-(isopropylidenedioxy)heptadecyl, 8,9:11,12-bis(isopropylidenedioxy)heptadecyl, 8,9:11,12:14,15-tris(isopropylidenedioxy)heptadecyl, 11,12-(isopropylidenedioxy)-8-heptadecenyl, 8-(6-hydroxyhexyloxy)octyl, 8-[2-(hexyloxy)ethoxy]octyl, 10-[2-(hexyloxy)ethoxy]decyl, 10-[2-(butoxy)ethoxy]decyl, 14-[2-(hexyloxy)ethoxy]tetradecyl, 14-[2-(2-hydroxyethoxy)ethoxy]tetradecyl, 14-[2-(butoxy)ethoxy]-tetradecyl, 14-[polyoxypropylene(5)]tetradecyl, 8-[6(2-hydroxyethoxy)hexyloxy]octyl, 11-[2-(2-hydroxyethoxy)ethoxycarbonyl]undecyl, 11-[2-(hexyloxy)ethoxy-carbonyl]undecyl, and 11-acetoxy-8-heptadecenyl.

Of these, preferred as R$^7$ are branched or cyclic, saturated C$_{7-25}$ hydrocarbons or groups represented by the following formula:

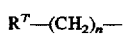

wherein R$^{7'}$ represents a C$_{6-15}$ hydrocarbon group containing one or more double bonds, hydroxyl groups, or ether groups, and n stands for an integer of 7–15.

Examples of the particularly preferred group include, but are not limited to methyl-branched isoheptadecyl, 8-heptadecyl, 8-heptadecenyl, 8,11-heptadecadienyl, 8,11,14-heptadecatrienyl, 11-hydroxyundecyl, 14-hydroxytetradecyl, 15-hydroxypentadecyl, 11-hydroxyheptadecyl, 11-hydroxy-8-heptadecenyl, 8,9-dihydroxyheptadecyl, 11,12-dihydroxy-8-heptadecenyl, 11-methoxyheptadecyl, 11-ethoxyheptadecyl, 11-benzyloxyheptadecyl, 11-methoxy-8-heptadecenyl, 11-benzyloxy-8-heptadecenyl, 8,9-(isopropylidenedioxy)heptadecyl, 8,9:11,12:14,15-tris(isopropylidenedioxy)heptadecyl, 11,12-(isopropylidenedioxy)-8-heptadecenyl, 8-(6-hydroxyhexyloxy)octyl, 8-[2-(hexyloxy)ethoxy]octyl, 10-[2-(hexyloxy)ethoxy]decyl, 10-[2-(butoxy)ethoxy]decyl, 14-[2-(hexyloxy)ethoxy]tetradecyl, 14-[2-(2-hydroxyethoxy)ethoxy]tetradecyl, 8-[6-(2-hydroxyethoxy)hexyloxy]octyl, 14-[2-(butoxy)ethoxy]tetradecyl, 14-[polyoxypropylene(5)]tetradecyl and the like.

R$^8$ and R$^9$ are the same or different and individually represent a hydrogen atom or a linear, branched, or cyclic C$_{1-40}$-hydrocarbon group which may contain one or more oxygen atoms; or R$^8$ and R$^9$ are coupled together to form a divalent C$_{1-40}$ hydrocarbon group, which may contain one or more oxygen atoms. As the linear, branched or cyclic C$_{1-40}$ hydrocarbon group which may contain one or more oxygen atoms, either a saturated or unsaturated hydrocarbon group can be used.

Examples include, but are not limited to hydrocarbon groups which may be substituted by one or more hydroxyl, alkoxyl, hydroxyalkoxyl, alkenyloxy, hydroxyalkenyloxy, aralkyloxy, alkylidenedioxy, polyoxyalkylene, acyl, acyloxy and the like.

Specific examples of such a hydrocarbon group include, but are not limited to methyl, ethyl, propyl, isopropyl, butyl, hexyl, octyl, decyl, dodecyl, tetradecyl, hexadecyl, octadecyl, icosyl, dotriacontyl, isostearyl, 2-ethylhexyl, 9-octacdecenyl, 9,12-octadecadienyl, 9,12,16-octadecatrienyl, cholesteryl, 2-hydroxyethyl, 3-hydroxypropyl, 11-hydroxyundecyl, 12-hydroxydodecyl, 15-hydroxypentadecyl, 16-hydroxyhexadecyl, 12-hydroxyoctadecyl, 12-hydroxy-9-octadecenyl, 9,10-dihydroxyoctadecyl, 2-(2-hydroxyethoxy)ethyl, 2-methoxyethyl, 3-methoxypropyl, 12-methoxyoctadecyl, 12-ethoxyoctadecyl, 12-benzyloxyoctadecyl, 12-methoxy-9-octadecenyl, 12-benzyloxy-9-octadecenyl, 9,10-(isopropylidenedioxy)octadecyl, 15-(polyoxypropylene(5)] pentadecyl, 9-(6-hydroxyhexyloxy)nonyl, 3-hexadecyloxy-2-hydroxypropyl, cyclopentyl, cyclohexyl, cycloheptyl, phenyl, benzyl and the like. Of these, those having 1–21 carbon atoms are more preferred.

On the other hand, in the case where R$^8$ and R$^9$ are coupled together to form a divalent C$_{1-40}$ hydrocarbon group which may contain one or more oxygen atoms, either a saturated or unsaturated hydrocarbon group can be used as the hydrocarbon group. Preferred examples include divalent hydrocarbon groups each of which may be substituted by one or more hydroxyl, alkoxyl, hydroxyalkoxyl, alkenyloxy, hydroxyalkenyloxy, aralkyloxy, alkylidenedioxy, polyoxyalkylene, acyl, acyloxy and similar groups, with alkylene, alkenylene, alkylene-O-alkylene and alkenylene-O-alkenylene groups being more preferred. Specific examples include tetramethylene, pentamethylene, and 3-oxopentamethylene. Of these, those having 1–8 carbon atoms are more preferred.

Specific examples of the more preferred atom or group as R$^8$ or R$^9$ include, but are not limited to a hydrogen atom or a methyl, ethyl, propyl, isopropyl, butyl, hexyl, octyl, decyl, dodecyl, tetradecyl, hexadecyl, octadecyl, methyl-branched isostearyl, 2-ethylhexyl, 9-octadecenyl, 9,12-octadecadienyl, 9,12,16-octadecatrienyl, 2-hydroxyethyl, 3-hydroxypropyl, 11-hydroxyundecyl, 12-hydroxydodecyl, 15-hydroxypentadecyl, 16-hydroxyhexadecyl, 12-hydroxyoctadecyl, 12-hydroxy-9-octadecenyl, 9,10-dihydroxyoctadecyl, 2-(2-hydroxyethoxy)ethyl, 2-methoxyethyl, 3-methoxypropyl, 12-methoxyoctadecyl, 12-ethoxyoctadecyl, 12-benzyloxyoctadecyl, 12-methoxy-9-octadecenyl, 12-benzyloxy-9-octadecenyl, 9,10-(isopropylidenedioxy)octadecyl, 15-[polyoxypropylene-(5)]pentadecyl, 9-(6-hydroxyhexyloxy)nonyl, 3-hexadecyloxy-2-hydroxypropyl, cyclopentyl, cyclohexyl, cycloheptyl, phenyl and benzyl group.

$R^{10}$ represents a carbonyl group, methylene group or single bond. When $R^{10}$ represents a single bond, $R^{11}$ represents a hydrogen atom. Examples of, as $R^{11}$, the linear, branched or cyclic $C_{1-40}$ hydrocarbon group which may contain one or more oxygen atoms include hydrocarbon groups which may contain one or more hydroxyl groups (—OH), ether groups (—O—), carbonyl groups (C(=O)—), carboxyl groups (—COOH), or carboxylate groups (—COO—).

Specific examples of such a hydrocarbon group include, but are not limited to methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-heptacosyl, n-octacosyl, n-nonacosyl, n-triacontyl, n-hentriacontyl, n-dotriacontyl, n-tritriacontyl, n-tetratriacontyl, n-pentatriacontyl, n-hexatriacontyl, n-heptatriacontyl, n-octatriacontyl, n-nonatriacontyl, n-tetracontyl, 3-heptyl, 2,4,4-trimethylpentyl, 8-heptadecyl, isoheptadecyl, methyl-branched isoheptadecyl, 12-pentacosyl, cyclohexylethyl, 8-heptadecenyl, 8,11-heptadecadienyl, 8,11,14-heptadecatrienyl, cholesteryl, 8-hydroxyoctyl, 11-hydroxyundecyl, 14-hydroxytetradecyl, 15-hydroxypentadecyl, 111-hydroxyheptadecyl, 11-hydroxy-8-heptadecenyl, 8,9-dihydroxyheptadecyl, 11,12-dihydroxy-8-heptadecenyl, 11-methoxyheptadecyl, 11-ethoxyheptadecyl, 11-benzyloxyheptadecyl, 11-methoxy-8-heptadecenyl, 11-ethoxy-8-heptadecenyl, 11-benzyloxy-8-heptadecenyl, 9,10-(isopropylidenedioxy) decyl, 8,9-(isopropylidenedioxy)heptadecyl, 8,9:11,12-bis (isopropylidenedioxy)heptadecyl, 8,9:11,12:14,15-tris (isopropylidenedioxy)heptadecyl, 11,12-(isopropylidenedioxy)-8-heptadecenyl, 8-(6-hydroxyhexyloxy)octyl, 8[2-(hexyloxy)ethoxy]octyl, 10-[2-(hexyloxy)ethoxy]decyl, 10-(2-(butoxy)ethoxy]decyl, 14-[2-(hexyloxy)ethoxy]tetradecyl, 14-[2-(2-hydroxyethoxy)ethoxy]-tetradecyl, 14-[2-(butoxy)ethoxy]tetradecyl, 14-[polyoxypropylene(5)]tetradecyl, 8-[6-(2-hydroxyethoxy)hexyloxy]octyl, 11-[2-(2-hydroxyethoxy)ethoxycarbonyl]undecyl, 11-[2-(hexyloxy)ethoxycarbonyl]undecyl, 11-acetoxy-8-heptadecenyl and the like. Preferred are branched or cyclic, saturated $C_{7-25}$ hydrocarbon groups, or groups represented by the following formula:

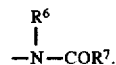

wherein $R^{11'}$ represents a $C_{6-15}$ hydrocarbon group containing one or more double bonds, hydroxyl groups, or ether groups, and m stands for an integer of 7–15.

Examples of the particularly preferred groups include, but are not limited to methyl-branched isoheptadecyl, 8-heptadecyl, 8-heptadecenyl, 8,11-heptadecadienyl, 8,11, 14-heptadecatrienyl, 11-hydroxyundecyl, 14-hydroxytetradecyl, 15-hydroxypentadecyl, 11-hydroxyheptadecyl, 11-hydroxy-8-heptadecenyl, 8,9-dihydroxyheptadecyl, 11,12-dihydroxy-8-heptadecenyl, 11-methoxyheptadecyl, 11-ethoxyheptadecyl, 11-benzyloxyheptadecyl, 11-methoxy-8-heptadecenyl, 11-benzyloxy-8-heptadecenyl, 8,9-(isopropylidenedioxy) heptadecyl, 8,9:11,12-bis(isopropylidenedioxy)heptadecyl, 8,9:11,12:14,15-tris(isopropylidenedioxy)heptadecyl, 11,12-(isopropylidenedioxy)-8-heptadecenyl, 8-(6-hydroxyhexyloxy)octyl, 8-[2-(hexyloxy)ethoxy]octyl, 10-[2-(hexyloxy)ethoxy]decyl, 10-[2-(butoxy)ethoxy]decyl, 14-[2-(hexyloxy)ethoxy]tetradecyl, 14-[2-(2-hydroxyethoxy)ethoxy]tetradecyl, 8-[6-(2-hydroxyethoxy)hexyloxy]octyl, 14[2-(butoxy)ethoxy)tetradecyl, 14-[polyoxypropylene(5)]tetradecyl.

In the amide derivative according to the present invention, the most preferred compounds are those in which are combined $R^1$, $R^2$, $R^3$, $R^4$, $R^5$, $R^6$, $R^7$, $R^8$, $R^9$, $R^{10}$ and $R^{11}$, each of which falling within the above particularly preferred range.

No particular limitation is imposed on the preparation process for the amide derivative of the present invention, but it is possible to synthesize it through the processes shown by the following reaction schemes.

(1) Process for the preparation of an amide derivative (1-A) represented by the formula (1) in which $R^5$ is $$\begin{array}{c} R^6 \\ | \\ -N-COR^7. \end{array}$$

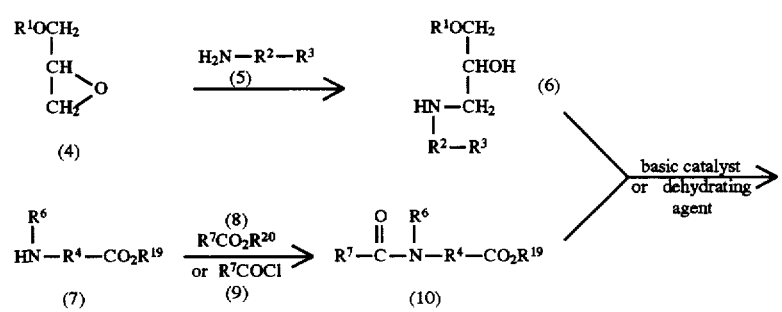

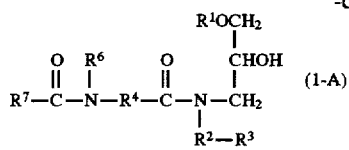

wherein $R^1$–$R^7$ have the same meanings as defined above and $R^{19}$ and $R^{20}$ each represents a hydrogen atom or a lower alkyl group.

In other words, a glycidyl ether compound (4) is reacted with an amine (5) to obtain an amino alcohol derivative (6). On the other hand, an aminocarboxylic acid derivative (7) is reacted with a carboxylic acid derivative (8) or an acid chloride (9) to obtain an amide carboxylic acid derivative (10). The compound (6) and the compound (10) so obtained are reacted in the presence of a dehydrating agent or a basic catalyst, whereby a target amide derivative (1-A) can be obtained.

Described specifically, the amide derivative (1-A) can be obtained as follows:

The amino alcohol derivative (6) can be obtained by reacting the glycidyl ether compound (4) with the amine (5) at a temperature ranging from room temperature to 150° C. without solvent, in water, or in a solvent, e.g., a lower alcohol such as methanol, ethanol or isopropanol, an ether-base solvent such as tetrahydrofuran, dioxane or ethylene glycol dimethyl ether, a hydrocarbon-base solvent such as hexane, benzene, toluene or xylene or a mixed solvent of any two or more of the above solvents.

On the other hand, the amide carboxylic acid derivative (10) can be obtained by reacting the aminocarboxylic acid derivative (7) with the carboxylic acid derivative (8) or the acid chloride (9) in the presence of a base, e.g., a tertiary amine such as pyridine or triethylamine, an acid, or a dehydrating agent such as dicyclohexylcarbodiimide, or in the absence thereof, without solvent or in a solvent, e.g., a halogenated hydrocarbon-base solvent such as chloroform, methylene chloride or 1,2-dichloroethane; an ether-base solvent such as tetrahydrofuran, dioxane or ethylene glycol dimethyl ether; a hydrocarbon-base solvent such as hexane, benzene, toluene or xylene; or a mixed solvent of any two or more of the above solvents.

The amide derivative (1-A) of the present invention can be obtained by reacting the amino alcohol derivative (6) with the amide carboxylic acid derivative (10) at from room temperature to 150° C., under reduced pressure of from normal pressure to 0.01 mmHg, in the presence of a dehydrating agent such as dicyclohexylcarbodiimide, or alternatively in the presence of a basic catalyst, e.g., an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, an alkali metal alcoholate such as sodium methoxide, sodium ethoxide or potassium tert-butoxide. Upon reaction, it is preferred to use the basic catalyst in an amount of 0.01 to 0.2 equivalents relative to the amino alcohol derivative (6). It is also preferred, for acceleration of the reaction, to conduct the reaction while removing the resultant alcohol from the system.

(2) Process for the preparation of an amide derivative (1-B) represented by the formula (1) in which $R^5$ is $$-\text{CON}\begin{matrix}R^8\\R^9\end{matrix}$$

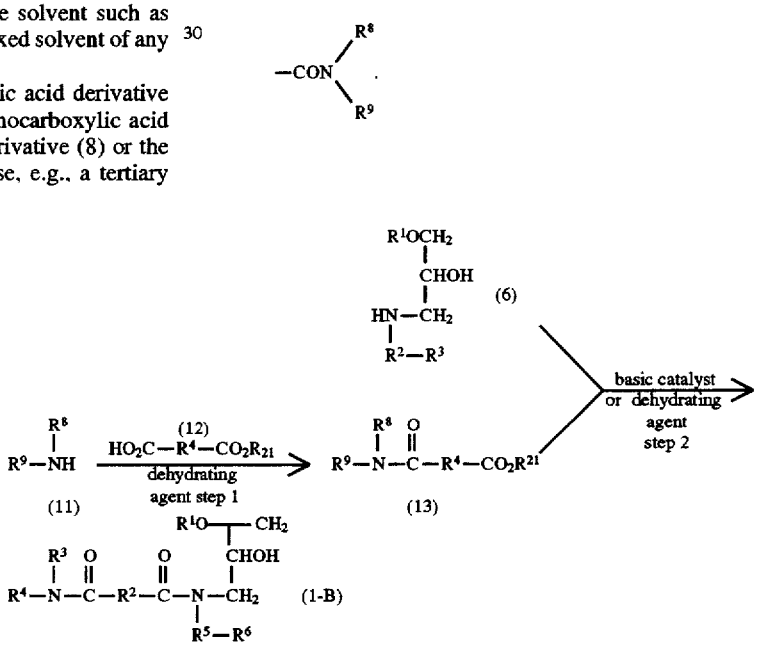

wherein $R^1$–$R^4$, $R^8$ and $R^9$ have the same meanings as defined above, and $R^{21}$ represents a hydrogen atom or a lower alkyl group.

Described specifically, an amine (11) is reacted with a dicarboxylic acid derivative (12) in the presence of a dehydrating agent, whereby a carboxylic acid derivative (13) is obtained (step 1). The compound (6) obtained in the above process (1) and the compound (13) are reacted in the presence of a dehydrating agent or a basic catalyst, whereby a target amide derivative (1-B) can be obtained (step 2).

The reaction in each step is as follows:

Step 1

The carboxylic acid derivative (13) can be obtained by reacting the amine (11) with the dicarboxylic acid derivative (12) in the presence or absence of a base, e.g., a tertiary amine such as pyridine or triethylamine, in the presence of a dehydrating agent such as dicyclohexylcarbodiimide with or without a solvent, e.g., a halogenated hydrocarbon-base solvent such as chloroform, methylene chloride or 1,2-dichloroethane; an ether-base solvent such as tetrahydrofuran, dioxane or ethylene glycol dimethyl ether, a hydrocarbon-base solvent such as hexane, benzene, toluene or xylene, or a mixed solvent of any two or more of the above solvents.

Step 2

The amide derivative (1-B) of the present invention can be obtained by reacting the amino alcohol derivative (6) thus prepared and the carboxylic acid derivative (13) at room temperature to 150° C. under reduced pressure of from normal pressure to 0.01 mmHg in the presence of a dehydrating agent such as dicyclohexylcarbodiimide, or alternatively in the presence of a base, e.g., an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, an alkali metal alcoholate such as sodium methoxide, sodium ethoxide or potassium tert-butoxide. Upon reaction, it is preferred to use the basic catalyst in an amount of 0.01 to 0.2 equivalent relative to the amino alcohol derivative (6). It is also preferred, for the acceleration of the reaction, to conduct the reaction while removing the resultant alcohol out of the system.

Alternatively, a compound containing $R^3$—$R^2$— and $R^1O$—$CH_2CH(OH)CH_2$— as $R^8$ and $R^9$, respectively, can be prepared by reacting the amine compound (6) with a di-lower alkyl dicarboxylate ($R^{21}OCO$—$R^4$—$COOR^{21}$). This reaction may be conducted in accordance with conventional amidation reaction methods.

(3) Process for the preparation of an amide derivative (1-C) represented by the formula (1) in which $R^{10}$ is a single bond ($R^{11}$ is a hydrogen atom).

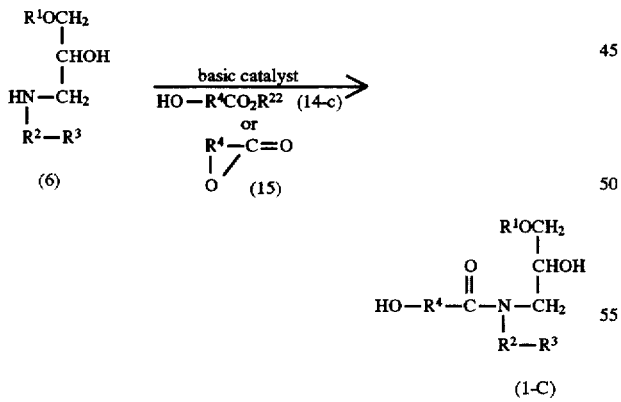

wherein $R^1$, $R^2$, $R^3$ and $R^4$ have the same meanings as defined in the above formula (1) and $R^{22}$ represents a $C_{1-5}$ alkyl group.

Described specifically, the amide derivative (1-C) can be prepared by acting a lower alkyl ester (14-c) of a hydroxy fatty acid or a hydroxy fatty acid lactone (15) on the amine derivative (6) in the presence of a basic catalyst, while distilling off the resultant lower alcohol.

(4) Process for the preparation of an amide derivative (1-D) represented by the formula (1) in which $R^{10}$ is a methylene (—$CH_2$—) group.

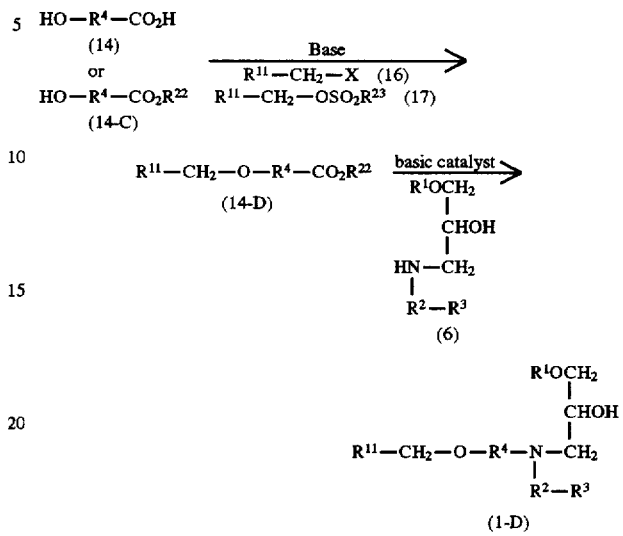

wherein $R^1$, $R^2$, $R^3$, $R^4$ and $R^{11}$ have the same meanings as defined in the above formula (1), $R^{22}$ represents a $C_{1-5}$ alkyl group, $R^{23}$ represents a methyl, phenyl or p-toluyl group and X represents a chlorine, bromine or iodine atom.

Described specifically, the amide derivative (1-D) can be obtained by reacting a hydroxy fatty acid (14) or a hydroxy fatty acid ester (14-C) with an alkyl halide (16) or an alkyl sulfonate (17) in the presence of a base to obtain an etherified fatty acid ester (14-D), then acting an amine derivative (6) on the ester (14-D) in the presence of a basic catalyst, while distilling off the resultant alcohol.

(5) Process for the preparation of an amide derivative (1-E) represented by the formula (1) in which $R^{10}$ is a carbonyl group (—C(=O)—) group.

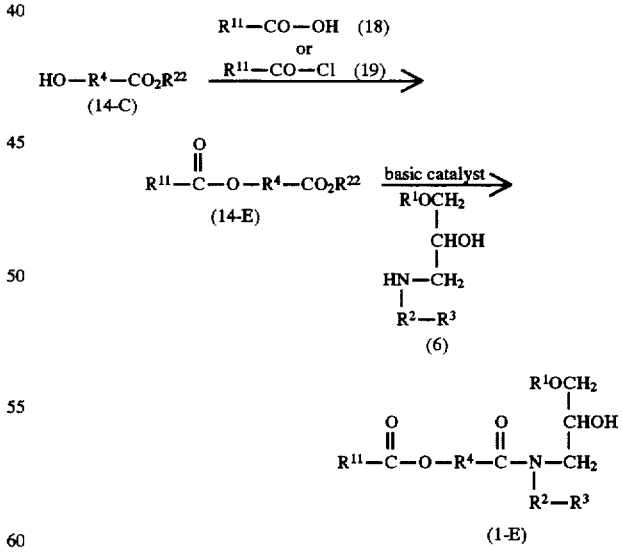

wherein $R^1$, $R^2$, $R^3$, $R^4$, $R^{11}$ and $R^{12}$ have the same meanings as defined above.

Described specifically, the amide derivative (1-E) can be obtained by condensing a hydroxy fatty acid ester (14-C) and a fatty acid (18) in the presence of a suitable dehydrating agent, e.g.,

13

 and P(C₆H₅)₃, to obtain an acyl fatty acid ester (5-E), or by reacting the hydroxy fatty acid ester (14-C) with a carboxylic acid chloride (19) to obtain the acyl fatty acid ester (5-E), acting the ester (5-E) on an amine derivative (6) obtained in the manner as described in Process 1 in the presence of a basic catalyst, while distilling off the resultant alcohol.

The amide derivative (1) of the present invention obtained in such a manner penetrates into lipid membranes in lipid-containing intercellular spaces between strata corneum (intercellular lipids), thereby improving, i.e., maintaining and reinforcing, the barrier function of the stratum corneum.

The amide derivative (1) of the present invention can be purified in a manner known to date. When incorporated in a composition for topical application to human skin, the amide derivative (1) of the present invention can be used either in the form of a product purified to have 100% purity, or in the form of a purification-free mixture containing an intermediate and/or reaction by-product, and having a purity of from 70% to 100%. In either case, excellent effects and performance can be attained and there is no problem in safety. The invention compound includes those in the form of a solvate typified by a hydrate.

The composition for topical application to human skin according to the present invention can be obtained by adding the amide derivative (1) of the present invention to a base (i.e., carrier) used for the conventional external compositions. The usage thereof can be classified roughly into medicinal dermatologic external compositions and cosmetics.

Examples of the medicinal dermatologic external composition include various ointments. As the ointment, either one in the form composed of an oily base or a water-in-oil or oil-in-water emulsion base can be used. There is no particular limitation on the oily base and examples include, but are not limited to vegetable oil, animal oil, synthetic oil, fatty acid, natural and synthetic glycerides and the like. No particular limitation is imposed on the pharmaceutically effective ingredient, and an analgesic antiinflammatory agent, antipruritic, disinfectant, antiseptic, astringent, skin softening agent, hormone or the like can be used, for example, as needed.

When used as a cosmetic composition, on the other hand, generally-employed cosmetic ingredients, e.g., an oil, surfactant, moisturizing agent, ultraviolet absorber, skin beautifier, alcohol, chelating agent, pH regulator, antiseptic, thickener, colorant or perfume, can be added in any combination to the amide derivative (1) of the present invention, which is an essential ingredient.

As cosmetic composition, it can be used in various forms such as water-in-oil or oil-in-water emulfisied cosmetic composition, cream, milky lotion, beauty wash, oily cosmetic composition, lip stick, foundation, skin wash, hair tonic, hair conditioner, hair rinse, hair treatment, hair growth accelerator or the like.

No particular limitation is imposed on the amount of the amide derivative (1) in the composition for topical application to human skin according to the present invention. In the case of an emulsion-type composition, 0.001–50 wt. % (wt. % is hereinafter referred to simply as "%") based on the total amount of the composition is preferred, 0.01–40% is more preferred, 0.5–20% is even more preferred. In the case of an oily composition employing as a base a liquid hydrocarbon such as squalane, 0.01–50% based on the total weight of the composition is preferred, 0.1–40% is more preferred, 0.5–20% is even more preferred.

The present invention will next be described in detail by the following examples. It should however be borne in mind that this invention is by no means limited to or by the examples.

EXAMPLES

EXAMPLE 1

Preparation of an amide derivative (1-a) represented by the formula (1) in which R⁵ represents

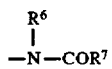

and R¹ through R⁷ represent the following groups, respectively:
$R^1$: $C_{16}H_{33}$—
$R^2$: —$(CH_2)_3$—
$R^3$: $CH_3O$—
$R^4$: —$(CH_2)_{11}$—

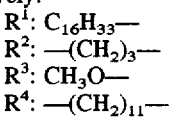

$R^6$: H

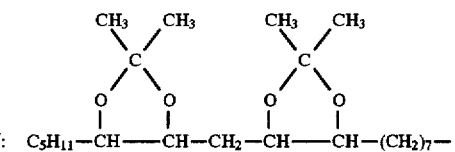

1-(1) Preparation of N-(3-hexadecyloxy-2-hydroxypropyl)-N-3-methoxypropylamine (6-a).

To a 2-l flask equipped with a stirrer, a dropping funnel, a nitrogen gas inlet tube and a distillation apparatus, 743.2 g (8.34 mol) of 3-methoxypropylamine (5-a) and 150 ml of ethanol were charged, followed by the dropwise addition of 165.9 g (0.56 mol) of hexadecyl glycidyl ether (4-a) over 3 hours while stirring under heating to 80° C. in a nitrogen atmosphere. After the completion of the dropwise addition, stirring was conducted for further 2 hours at 80° C. From the reaction mixture, ethanol and excessive 3-methoxypropylamine were distilled off by heating under reduced pressure. The residue was purified by chromatography on a silica gel column, whereby 196.5 g of the title compound (6-a) were obtained in the form of a white solid (yield: 91% relative to hexadecyl glycidyl ether).

1-(2) Preparation of 9,10:12,13-bis(isopropylidenedioxy) octadecanoic acid (8-a).

To a 2-l flask equipped with a stirrer, 147.2 g (0.5 mol) of methyl linoleate, 203.2 g (1.18 mol) of metachloroperbenzoic acid and 500 ml of dichloromethane were charged, followed by stirring at room temperature for 18 hours. After the completion of the reaction, the methachlorobenzoic acid thus precipitated was filtered off, followed by washing with an aqueous solution of sodium thiosulfate. The solvent was then distilled off under reduced pressure. The residue was purified by chromatography on an alumina short column, whereby methyl 9,10:12,13-diepoxyoctadecanoate was obtained.

Next, to a 2-l flask equipped with a stirrer and a dropping funnel, 1,162 g (20 mol) of acetone and 3.55 g (25 mmol) of a boron trifluoride-ether complex were charged, followed by the dropwise addition of the above-obtained methyl 9,10:12,13-diepoxyoctadecanoate over 3 hours under stirring at room temperature. After the completion of the dropwise addition, stirring was conducted for further one hour to complete the reaction. Sodium bicarbonate was then added to the reaction mixture for neutralization and then, the solvent was distilled off under reduced pressure. The residue was purified by chromatography on a silica gel column, whereby 201.2 g of methyl 9,10:12,13-bis(isopropylidenedioxy)octadecanoate were obtained (yield: 91%).

In a 2-l flask equipped with a stirrer, 141.6 g (0.32 mol) of the above-obtained methyl 9,10:12,13-bis(isopropylidenedioxy)octadecanoate and 400 ml of ethanol were charged, followed by the addition of a solution mixture composed of a solution of 35.8 g (0.64 mol) of potassium hydroxide dissolved in 40 ml of water and 400 ml of ethanol. The resulting mixture was stirred at 50° C. for one hour. The reaction mixture was then neutralized with hydrochloric acid, followed by extraction with chloroform. The solvent was then distilled off under reduced pressure and the residue was purified by chromatography on a silica gel column, whereby 132.0 g of the title compound (8-a) were obtained (yield: 96%).

1-(3) Preparation of methyl 12-aminododecanoate (7-a).

To a 3-l flask equipped with a stirrer, 200.0 g (0.93 mol) of 12-aminododecanoic acid, 600 g of methanol and 100 g (1.0 mol) of sulfuric acid were charged, followed by stirring at 60° C. for 5 hours. After the reaction mixture was allowed to cool down, it was diluted with methylene chloride, followed by neutralization with an aqueous solution of sodium carbonate. The solvent was distilled off under reduced pressure, followed by purification by chromatography on an alumina short column, whereby 201.7 g of the title compound (7-a) were obtained (yield: 95%).

1-(4) Preparation of methyl 12-[9,10:12,13-bis(isopropylidenedioxy)octadecanoylamino]dodecanoate (10-a).

To a 1-l flask equipped with a stirrer, 34.3 g (80 mmol) of the compound (8-a) obtained in the above (2), 22.9 g (100 mmol) of the compound obtained in the above (3), 18.4 g (120 mmol) of 1-hydroxybenzotriazole and 500 ml of chloroform were charged, followed by the addition of 33.0 g of N,N'-dicylohexylcarbodiimide under stirring at room temperature. Stirring was conducted for further 24 hours at room temperature. After the completion of the reaction, the white solid thus precipitated was filtered off from the reaction mixture, followed by concentration under reduced pressure. The residue was purified by chromatography on a silica gel column, whereby 33.1 g of the title compound (10-a) were obtained (yield: 68%).

1-(5) Preparation of an amide derivative (1-a).

To a 100-ml flask equipped with a stirrer, a dropping funnel and a distillation apparatus, 11.6 g (30 mmol) of the compound (6-a) obtained in the above (1) and 20.1 g (33 mmol) of the compound (10-a) obtained in the above (4) were charged, followed by the dropwise addition of 0.58 g (3 mmol) of 28% methanol solution of sodium methoxide while stirring at 80° C. under an $N_2$ atmosphere. After the completion of the dropwise addition, stirring was conducted at 80° C. for one hour, followed by stirring at 80° C. under reduced pressure (10 Torr) for further six hours to complete the reaction. After cooling, the reaction mixture was purified by chromatography on a silica gel column, whereby 25.6 g of the target amide derivative (1-a) were obtained (yield: 88%).

The amide derivative (1-a) so obtained has the following physical properties:

Pale yellow solid. Melting point: 46°–48° C. IR(KBr, cm$^{-1}$): 3350, 2940, 2880, 1615, 1540, 1465, 1380, 1215, 1110, 720. $^1$H-NMR(CDCl$_3$, δ): 0.88 (br t, J=6.4 Hz, 6H), 1.10–2.05 (m, 82H), 2.15 (t, J=7.5 Hz, 2H), 2.38 (t, J=7.5 Hz, 2H), 3.15–4.20 (m, 18H), 3.33 (s, 3H), 5.35–5.50 (m, 1H).

EXAMPLE 2

Preparation of an amide derivative (1-b) represented by the formula (1) in which R$^5$ represents

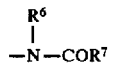

and R$^1$ through R$^7$ represent the following groups, respectively:

R$^1$: C$_{16}$H$_{33}$—
R$^2$: —(CH$_2$)$_2$—
R$^3$: CH$_3$O—
R$^4$: —(CH$_2$)$_{11}$—

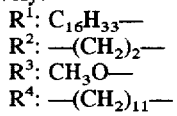

R$^6$: H
R$^7$: C$_5$H$_{11}$—CH=CH—CH$_2$—CH=CH—(CH$_2$)$_7$—

2-(1) Preparation of N-(3-hexadecyloxy-2-hydroxypropyl)-N-2-methoxyethylamine (6-b).

In a similar manner to Example 1 (1), except for the use of 2-methoxyethylamine (5-b) instead of 3-methoxypropylamine (5-a), the title compound (6-b) was obtained.

2-(2) Preparation of methyl 12-linoleoylaminododecanoate (10-b).

To a 1-l flask equipped with a stirrer, a dropping funnel and a nitrogen gas inlet tube, 45.9 g (200 mmol) of the compound (7-a) obtained above in Example 1-(3), 30.4 g (300 mmol) of triethylamine and 300 g of methylene chloride were charged, followed by the dropwise addition of 65.8 g (220 mmol) of linoleoyl acid chloride over one hour while stirring at room temperature. After the completion of the dropwise addition, stirring was conducted for further one hour at room temperature to complete the reaction.

The reaction mixture so obtained was then washed with saturated saline, followed by concentration under reduced pressure. The residue was purified by chromatography on a silica gel column, whereby 88.3 g of the title compound (10-b) were obtained (yield: 90%).

2-(3) Preparation of an amide derivative (1-b).

In a similar manner to Example 1-(5), except that the compound (6-b) obtained in the above (1) and the compound (10-b) obtained in the above (2) were used instead of the compound (6-a) and the compound (10-a), respectively, the target amide derivative (1-b) was obtained.

The amide derivative (1-b) so obtained has the following physical properties:

White solid. Melting point: 56°–58° C. IR(KBr, cm$^{-1}$) 3320, 2925, 2860, 1640, 1615, 1545, 1470, 1210, 1110, 1060, 720. $^1$H-NMR(CDCl$_3$, δ): 0.80–1.00 (m, 6H), 1.10–1.80 (m, 62H) 1.95–2.15 (m, 4H), 2.15 (t, J=7.5 Hz, 2H), 2.30–2.50 (m, 2H), 2.70–2.90 (m, 2H), 3.15–4.05 (m, 17H), 2.50–5.50 (m, 5H).

EXAMPLE 3

Preparation of an amide derivative (1-c) represented by the formula (1) in which R$^5$ represents $$\overset{R^6}{\underset{|}{-N-COR^7}}$$

and $R^1$ through $R^7$ represent the following groups, respectively:

$R^1$: $C_{16}H_{33}-$
$R^2$: $-(CH_2)_2-$
$R^3$: $HO-(CH_2)_2O-$
$R^4$: $-(CH_2)_{11}-$ $R^5$: $\overset{R^6}{\underset{|}{-N-COR^7}}$ $R^6$: H
$R^7$: $C_5H_{11}-CH=CH-CH_2-CH=CH-(CH_2)_7-$ 3-(1) Preparation of N-(3-hexadecyloxy-2-hydroxypropyl)-N-(2-(2-hydroxyethoxy)ethylamine (6-c).

In a similar manner to Example 1-(1), except for the use of 2-(2-aminoethoxy)ethanol (5-c) instead of the compound (5-a), the title compound (6-c) was obtained.

3-(2) Preparation of an amide derivative (1-c).

In a similar manner to Example 1-(5), except that the compound (6-c) obtained in the above (1) and the compound (10-b) obtained above in Example 2-(2) were used instead of the compound (6-a) and the compound (10-a), respectively, the target amide derivative (1-c) was obtained.

The amide derivative (1-c) so obtained has the following physical properties:

Colorless solid Melting point: 73°–74° C. IR(KBr, cm$^{-1}$): 3315, 2925, 2855, 1620, 1545, 1465, 1210, 1110, 1060, 720. $^1$H-NMR(CDCl$_3$, δ): 0.80–1.00 (m, 6H), 1.10–1.75 (m, 62H), 1.95–2.25 (m, 4H), 2.15 (t, J=7.6 Hz, 2H), 2.30–2.50 (m, 2H), 2.70–2.85 (m, 2H), 3.15–4.10 (m, 19H), 5.25–5.50 (m, 5H).

EXAMPLE 4

Preparation of an amide derivative (1-d) represented by the formula (1) in which $R^5$ represents $$\overset{R^6}{\underset{|}{-N-COR^7}}$$

and $R^1$ through $R^7$ represent the following groups, respectively:

$R^1$: $C_{16}H_{33}-$
$R^2$: $-(CH_2)_3-$
$R^3$: $CH_3O-$
$R^4$: $-(CH_2)_{11}-$ $R^5$: $\overset{R^6}{\underset{|}{-N-COR^7}}$ $R^6$: H $R^7$: $C_6H_{13}-\overset{OCH_3}{\underset{|}{CH}}-CH_2-CH=CH-(CH_2)_7-$ 4-(1) Preparation of 12-methoxy-9-octadecenoic acid (8-d).

To a 1-l flask equipped with a stirrer, a dropping funnel and a condenser, 24 g (0.6 mol) of 60% sodium hydride, 500 ml of dimethylformamide were charged, followed by the dropwise addition of a solution of 163.3 g (0.5 mol) of ethyl ricinoleate in 142 g (1.0 mol) of methyl iodide over one hour while stirring at 40° C. under an N$_2$ atmosphere. After the completion of the dropwise addition, stirring was conducted at 40° for further 6 hours. To the reaction mixture so obtained, hexane was added. The resulting mixture was then washed with an aqueous solution of ammonium chloride and an aqueous solution of sodium thiosulfate, followed by concentration under reduced pressure. The residue was purified by chromatography on a silica gel column, whereby 155.8 g of ethyl 12-methoxy-9-octadecenoate were obtained (yield: 92%).

Next, to a 1-l flask equipped with a stirrer, 68.1 g (0.2 mol) of ethyl 12-methoxy-9-octadecenoate, 600 ml of ethanol and 45 g of a 50% aqueous solution of potassium hydroxide were charged, followed by stirring at 50° C. for 4 hours. To the reaction mixture so obtained, hexane was added, followed by neutralization with 3N hydrochloric acid and then washing with saturated saline. After concentration under reduced pressure, the residue was purified by chromatography on a silica gel column, whereby 58.3 g of the title compound (8-d) were obtained (yield: 93%).

4-(2) Preparation of an amide derivative (1-d).

In a similar manner to Example 1-(4) and 1-(5), except that the compound (8-d) obtained in the above (1) was used instead of the compound (8-a), the target amide derivative (1-d) was obtained.

The amide derivative (1-d) so obtained has the following physical properties:

White solid. Melting point: 56°–58° C. IR(KBr, cm$^{-1}$): 3310, 2900, 1610, 1545, 1470, 1110, 950, 720. $^1$H-NMR (CDCl$_3$, δ): 0.88 (br t, J=6.4 Hz, 6H), 1.10–1.78 (m, 66H), 1.83 (t, J=6.0 Hz, 2H), 1.95–2.10 (m, 2H), 2.15 (t, J=7.6 Hz, 2H), 2.18–2.30 (m, 2H), 2.36 (t, J=7.5 Hz, 2H), 3.10–3.60 (m, 14H), 3.33 (s, 3H), 3.34 (s, 3H), 3.85–4.05 (m, 1H), 5.30–5.60 (m, 3H).

EXAMPLE 5

Preparation of an amide derivative (1-e) represented by the formula (1) in which $R^5$ represents $$\overset{R^6}{\underset{|}{-N-COR^7}}$$

and $R^1$ through $R^7$ represent the following groups, respectively:

$R^1$: $C_{16}H_{33}-$
$R^2$: $-(CH_2)_2-$
$R^3$: $HO-(CH_2)_2O-$
$R^4$: $-(CH_2)_{11}-$ $R^5$: $\overset{R^6}{\underset{|}{-N-COR^7}}$ $R^6$: H $R^7$: $C_6H_{13}-\overset{OCH_3}{\underset{|}{CH}}-CH_2-CH=CH-(CH_2)_7-$ In a similar manner to Example 1-(4) and 1-(5), except that the compound (8-d) obtained in Example 4-(1) was used instead of the compound (8-a) and the compound (6-c) obtained in Example 3-(1) was used instead of the compound (6-a), the target amide derivative (1-e) was obtained.

The amide derivative (1-e) so obtained has the following physical properties:

White solid. Melting point: 69°–70° C. IR(KBr, cm$^{-1}$): 3310, 2895, 2870, 1605, 1540, 1460, 1105, 720. $^1$H-NMR (CDCl$_3$, δ): 0.80–0.97 (m, 6H), 1.10–1.80 (m, 66H), 1.95–2.30 (m, 4H), 2.15 (t, J=7.7 Hz, 2H), 2.30–2.50 (m, 2H), 3.10–4.15 (m, 20H), 3.34 (s, 3H), 5.35–5.55 (m, 3H).

EXAMPLE 6

Preparation of an amide derivative (1-f) represented by the formula (1) in which $R^5$ represents

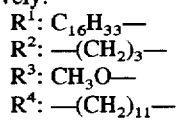

and $R^1$ through $R^7$ represent the following groups, respectively:
$R^1$: $C_{16}H_{33}$—
$R^2$: —$(CH_2)_3$—
$R^3$: $CH_3O$—
$R^4$: —$(CH_2)_{11}$—

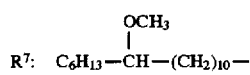

$R^6$: H

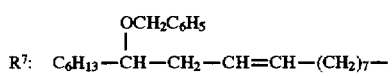

To a 1-l flask equipped with a stirrer and a hydrogen gas inlet tube, 9.1 g (10.3 mmol) of the compound (1-d) prepared in Example 4, 1.5 g of 5% palladium carbon and 370 ml of ethanol were charged, followed by stirring at room temperature for 22 hours under a hydrogen atmosphere. The reaction mixture so obtained was filtered and the filtrate was concentrated under reduced pressure. The residue was purified by chromatography on a silica gel column, whereby 9.06 g of the target amide derivative (1-f) were obtained (yield: 99%).

The amide derivative (1-f) so obtained has the following physical properties:

White solid. Melting point: 58°–60° C. IR(KBr, cm$^{-1}$): 3330, 2920, 1630, 1550, 1470, 1205, 1110, 720. $^1$H-NMR (CDCl$_3$, δ): 0.88 (br t, J=6.2 Hz, 6H), 1.05–1.80 (m, 74H), 1.83 (t, J=5.9 Hz, 2H), 2.15 (t, J=7.6 Hz, 2H), 2.36 (t, J=7.5 Hz, 2H), 3.05–3.60 (m, 14H), 3.31 (s, 3H), 3.33 (s, 3H), 3.85–4.00 (m, 1H), 5.35–5.50 (m, 1H).

EXAMPLE 7

Preparation of an amide derivative (1-g) represented by the formula (1) in which $R^5$ represents

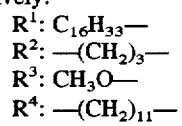

and $R^1$ through $R^7$ represent the following groups, respectively:
$R^1$: $C_{16}H_{33}$—
$R^2$: —$(CH_2)_3$—
$R^3$: $CH_3O$—
$R^4$: —$(CH_2)_{11}$—

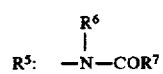

$R^6$: H

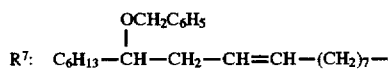

7-(1) Preparation of 12-benzyloxy-9-octadecenoic acid (8-g).

In a similar manner to Example 4 (1), benzyl bromide was used instead of methyl iodide, the title compound (8-g) was obtained.

7-(2) Preparation of an amide derivative (1-g).

In a similar manner to Example 1-(4) and (5), except that the compound (8-g) obtained in the above (1) was used instead of the compound (8-a), the target amide derivative (1-g) was obtained.

The amide derivative (1-g) so obtained has the following physical properties;

White solid. Melting point: 56°–58° C. IR(KBr, cm$^{-1}$): 3335, 2900, 1625, 1550, 1470, 1105, 720. $^1$H-NMR(CDCl$_3$, δ) : 0.88 (br t, J=6.4 Hz, 6H), 1.10–1.75 (m, 66H), 1.83 (t, J-5.9 Hz, 2H), 1.95–2.10 (m, 2H), 2.14 (t, J=7.6 Hz, 2H), 2.25–2.45 (m, 2H), 2.37 (t, J=7.6 Hz, 2H), 3.15–3.60 (m, 14H), 3.33 (s, 3H), 3.85–4.00 (m, 1H), 4.53 (dd, J=11.7 Hz, 20.0 Hz, 2H), 5.30–5.55 (m, 3H), 7.20–7.45 (m, 5H).

EXAMPLE 8

Preparation of an amide derivative (1-h) represented by the formula (1) in which $R^5$ represents

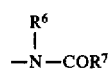

and $R^1$ through $R^7$ represent the following groups, respectively:
$R^1$: C
$R^2$: —$(CH_2)_2$—
$R^3$: HO—$(CH_2)_2O$—
$R^4$: —$(CH_2)_{11}$—

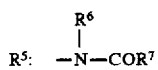

$R^6$: H

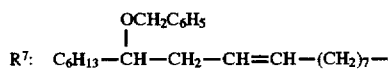

In a similar manner to Example 1-(4) and (5), the compound (8-g) obtained in Example 7-(1) was used instead of the compound (8-a) and the compound (6-c) obtained in Example 3-(1) was used instead of the compound 6(a), the target amide derivative (1-h) was obtained.

The amide derivative (1-h) so obtained has the following physical properties:

White solid. Melting point: 70°–71° C. IR(KBr, cm$^{-1}$): 3330, 2900, 1630, 1615, 1545, 1470, 1110, 720. $^1$H-NMR (CDCl$_3$, δ): 0.88 (br t, J=6.4 Hz, 6H), 1.10–1.80 (m, 66H), 1.95–2.15 (m, 2H), 2.14 (t, J=7.6 Hz, 2H), 2.25–2.40 (m, 2H), 2.38 (t, J=7.4 Hz, 2H), 3.15–3.85 (m, 18H), 3.85–4.20 (m, 2H), 4.53 (dd, J=11.7 Hz, 19.9 Hz, 2H), 5.27–5.55 (m, 3H), 7.25–7.40 (m, 5H).

EXAMPLE 9

Preparation of an amide derivative (1-i) represented by the formula (1) in which $R^5$ represents

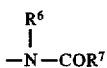

and R$^1$ through R$^7$ represent the following groups, respectively:

R$^1$: C$_{16}$H$_{33}$—
R$^2$: —(CH$_2$)$_3$—
R$^3$: CH$_3$O—
R$^4$: —(CH$_2$)$_{11}$—

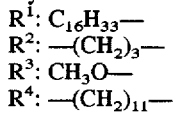

R$^6$: H

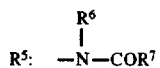
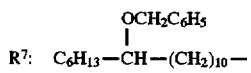

9-(1) Preparation of 12-benzyloxy-octadecanoic acid (8-i).

In a similar manner to Example 4-(1), methyl 12-hydroxyoctadecanoate was used instead of ethyl ricinoleate and benzyl bromide was used instead of methyl iodide, the title compound (8-i) was obtained.

9-(2) Preparation of an amide derivative (1-i).

In a similar manner to Example 1-(4) and (5), except that the compound (8-i) obtained in the above (1) was used instead of the compound (8-a), the target amide derivative (1-i) was obtained.

The amide derivative (1-i) so obtained has the following physical properties:

White solid. Melting point: 59°–61° C. IR(KBr, cm$^{-1}$): 3320, 2900, 1615, 1545, 1470, 1100, 720. $^1$H-NMR(CDCl$_3$, δ): 0.88 (br t, J=6.5 Hz, 6H), 1.00– 1.95 (m, 76H), 2.15 (t, J=7.5 Hz, 2H), 2.36 (t, J=7.5 Hz, 2H), 3.15–3.60 (m, 14H), 3.33 (s, 3H), 3.85–4.00 (m,$_1$H), 4.50 (s, 2H), 5.35–5.50 (m, 1H), 7.20–7.45 (m, 5H).

EXAMPLE 10

Preparation of an amide derivative (1-j) represented by the formula (1) in which R$^5$ represents

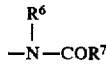

and R$^1$ through R$^7$ represent the following groups, respectively:

R$^1$: C$_{16}$H$_{33}$—
R$^2$: —(CH$_2$)$_3$—
R$^3$: CH$_3$O—
R$^4$: —(CH$_2$)$_{11}$—

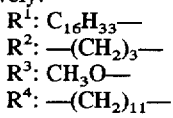

R$^6$: H

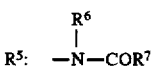
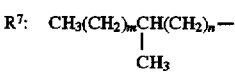

wherein m+n=10–16, m=4–10, n=4–10, and m and n stand for numbers having distribution with m=7 and n=7 as peaks, respectively.

10-(1) Preparation of methyl methyl-branched isostearoylaminododecanoate (10-j).

In a similar manner to Example 2-(2), methyl-branched isostearic acid chloride (7-j) was used instead of linoleoyl acid chloride (9-b), the title compound (10-j) was obtained.

10-(2) Preparation of an amide derivative (1-j).

In a similar manner to Example 1-(5), except that the compound (10-j) obtained in the above (1) was used instead of the compound (10-a), the target amide derivative (1-j) was obtained.

The amide derivative (1-j) so obtained has the following physical properties:

White solid. Melting point: 60°–63° C. IR(KBr, cm$^{-1}$): 3415, 3330, 2940, 2860, 2330, 1645, 1615, 1550, 1470, 1380, 1215, 1100, 1050, 720. $^1$H-NMR(CDCl$_3$, δ): 0.75–0.98 (m, 9H), 0.98–1.80 (m, 73H) 1.83 (t, J=5.7 Hz, 2H), 2.15 (t, J=7.6 Hz, 2H), 2.37 (t, J=7.5 Hz, 2H), 3.15–3.60 (m, 13H), 3.33 (s, 3H), 3.80–4.00 (m, 1H), 5.35–5.50 (m, 1H).

EXAMPLE 11

Preparation of an amide derivative (1-k) represented by the formula (1) in which R$^5$ represents

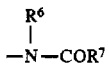

and R$^1$ through R$^7$ represent the following groups, respectively:

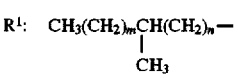

R$^2$: —(CH$_2$)$_2$—
R$^3$: H
R$^4$: —(CH$_2$)$_{11}$—

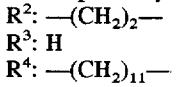

R$^6$: H

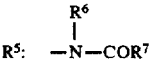
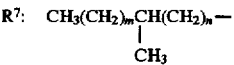

wherein m+n=10–16, m=4–10, n=4–10, and m and n stand for numbers having distribution with m=7 and n=7 as peaks, respectively.

11-(1) Preparation of N-(3-methyl-branched isostearoxy-2-hydroxypropyl)-N-ethylamine (6-k).

In a similar manner to Example 1-(1), except that ethylamine (5-k) was used instead of 3-methoxypropylamine (5-a) and methyl-branched isostearylglycidylether (4-k) was used instead of hexadecylglycidylether (4-a), the title compound (6-k) was obtained.

11-(2) Preparation of an amide derivative (1-k).

In a similar manner to Example 1-(5), except that the compound (6-k) obtained in the above (1) was used instead of the compound (6-a) and the compound (10-j) obtained in Example 10-(1) was used instead of the compound (10-a), the target amide derivative (1-k) was obtained.

The amide derivative (1-k) so obtained has the following physical properties:

White solid. Melting point: 61°–64° C. IR(KBr, cm$^{-1}$): 3400, 2930, 2865, 1625, 1540, 1470, 1380, 1230, 1210, 1110, 720. $^1$H-NMR(CDCl$_3$, δ): 0.75–1.00 (m, 12H), 1.00–1.85 (m, 77H), 2.15 (t, J=7.6 Hz, 2H), 2.35 (t, J=7.6 Hz, 2H), 3.15–3.60 (m, 11H), 3.80–4.00 (m, 1H), 5.35–5.50 (m, 1H).

EXAMPLE 12

Preparation of an amide derivative (1-l) represented by the formula (1) in which $R^5$ represents

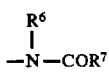

and $R^1$ through $R^7$ represent the following groups, respectively:

$R^1$: $C_{16}H_{33}$—
$R^2$: —(CH$_2$)$_3$—
$R^3$: CH$_3$O—
$R^4$: —(CH$_2$)$_{10}$—

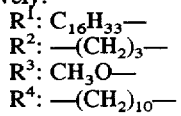

$R^6$: H

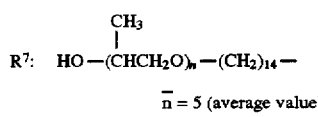

$\overline{n}$ = 5 (average value)

12-(1) Synthesis of a compound (8-l), a compound represented by the formula (8), in the before-described reaction scheme, wherein $R^7$ represents the following group

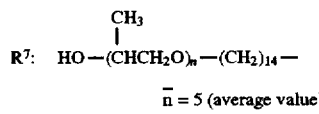

$\overline{n}$ = 5 (average value)

To a 200-ml flask equipped with a stirrer, a dropping funnel and a condenser, 10.0 g (33.9 mmol) of isopropyl 15-hydroxypentadecanoate, 25 ml of dimethylformamide and 0.4 g (10 mmol) of 60% sodium hydride were charged, followed by the addition of 19.7 g (339 mmol) of propylene oxide and stirring at 100° C. for 18 hours. After the completion of the reaction, 8 g of a 50% aqueous solution of sodium hydroxide and 80 ml of ethanol were added, followed by stirring at 60° C. for one hour. The reaction mixture was cooled to room temperature, added with water, and then washed with hexane. After acidification with 3N hydrochloric acid, the acidified solution was extracted with isopropyl ether. The extract was concentrated under reduced pressure, whereby 17.0 g of the crudely-purified product of the title compound (8-l) were obtained (crude yield: 92%).

12-(2) Preparation of methyl 11-aminoundecanoate (7-l).

In a similar manner to Example 1 (3), except for the use of 11-aminoundecanoic acid instead of 12-aminododecanoic acid, the title compound (7-l) was obtained.

12-(3) Preparation of an amide derivative (1-l).

In a similar manner to Example 1-(4) and (5), except that the compound (8-l) obtained in the above (1) was used instead of the compound (8-a) and the compound (7-l) obtained in the above (2) was used instead of the compound (7-a), the target amide derivative (1-l) was obtained.

The amide derivative (1-l) so obtained has the following physical properties:

White solid. Melting point: 47°–55° C. IR(KBr, cm$^{-1}$): 3330, 2920, 1620, 1540, 1465, 1110, 720. $^1$H-NMR(CDCl$_3$, δ): 0.75–1.00 (m, 3H), 1.00–1.85 (m, about 83H), 1.85–2.05 (m, 4H), 2.15 (t, J=7.5 Hz, 2H), 2.30–2.50 (m, 2H), 3.10–4.40 (m, about 30H), 5.45–5.65 (m, 1H).

EXAMPLE 13

Preparation of an amide derivative (1-m) represented by the formula (1) in which $R^5$ represents

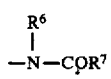

and $R^1$ through $R^7$ represent the following groups, respectively:

$R^1$: $C_{16}H_{33}$—
$R^2$: —(CH$_2$)$_3$—
$R^3$: CH$_3$O—
$R^4$: —(CH$_2$)$_{11}$—

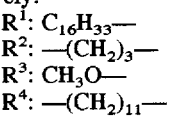

$R^6$: H $R^7$: $C_{17}H_{35}$—

13-(1) Preparation of methyl octadecanoylaminodecanoate (10-m).

In a similar manner to Example 2 (2), except for the use of octadecanoic acid chloride (9-m) instead of linoleic acid chloride (9-b), the title compound (10-m) was obtained.

13-(2) Preparation of an amide derivative (1-m).

In a similar manner to Example 1-(5), except that the compound (10-m) obtained in the above (1) was used instead of the compound (10-a), the target amide derivative (1-m) was obtained.

The amide derivative (1-m) so obtained has the following physical properties:

White solid. Melting point: 63°–64° C. IR(KBr, cm$^{-1}$): 3335, 2925, 1650, 1620, 1550, 1470, 1215, 1010, 720. $^1$H-NMR(CDCl$_3$, δ): 0.88 (br t, J=6.4 Hz, 6H), 1.05–1.75 (m, 76H), 1.83 (t, J=5.8 Hz, 2H), 2.15 (t, J=7.5 Hz, 2H), 2.36 (t, J=7.5 Hz, 2H), 3.153.60 (m, 13H), 3.33 (s, 3H), 3.85–4.00 (m, 1H), 5.305.60 (m, 1H).

EXAMPLE 14

Preparation of an amide derivative (1-n) represented by the formula (1) in which $R^5$ represents

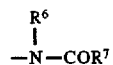

and $R^1$ through $R^7$ represent the following groups, respectively:

$R^1$: $C_4H_9$—
$R^2$: —(CH$_2$)$_3$—
$R^3$: CH$_3$O—
$R^4$: —(CH$_2$)$_{11}$—

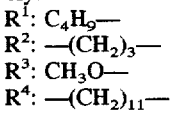

$R^6$: H
$R^7$: CH$_3$(CH$_2$)$_m$CHCH$_3$(CH$_2$)$_n$— wherein m+n=10–16, m=4–10, n=4–10, and m and n stand for numbers having distribution with m=7 and n=7 as peaks, respectively.

(1) Preparation of N-(3-butyloxy-2-hydroxypropyl)-N-3-methoxypropylamine (6-n)

In a similar manner to Example 1-(1) except that butylglycidyl ether (4-n) was used instead of hexadecylglycidyl ether (4-a), the title compound (6-n) was obtained.

(2) Preparation of an amide derivative (1-n)

In a similar manner to Example 1-(5) except that the compound (6-n) obtained in the above (1) was used instead of the compound (6-a) and the compound (10-j) obtained in Example 10-(1) was used instead of the compound (10-a), the target amide derivative (1-n) was obtained.

The amide derivative (1-n) so obtained has the following physical properties:

Colorless oil. IR(KBr, cm$^{-1}$): 3320, 2930, 2860, 1630, 1550, 1460, 1380, 1220, 1120, 750. $^1$H-NMR(CDCl$_3$, δ): 0.70–0.95 (m, 9H), 1.10–1.71 (m, 49H), 1.72–1.94 (m, 2H), 2.12 (t, J=7.6 Hz, 2H), 2.33 (t, J=7.6 Hz, 2H), 3.14–3.60 (m, 13H), 3.79–4.00 (m, 1H), 5.34–5.56 (m, 1H).

EXAMPLE 15

Preparation of an amide derivative (1-o) represented by the formula (1) in which R$^5$ represents

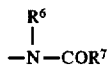

and R$^1$ through R$^7$ represent the following groups, respectively:

R$^1$: C$_8$H$_{17}$—
R$^2$: —(CH$_2$)$_3$—
R$^3$: CH$_3$O—
R$^4$: —(CH$_2$)$_{11}$—

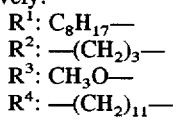

R$^6$: H
R$^7$: CH$_3$(CH$_2$)$_m$CHCH$_3$(CH$_2$)$_n$— wherein m+n=10–16, m=4–10, n=4–10, and m and n stand for numbers having distribution with m=7 and n=7 as peaks, respectively.

(1) Preparation of N-(3-octyloxy-2-hydroxypropyl)-N-3-methoxypropylamine (6-o)

In a similar manner to Example 1-(1) except that octylglycidyl ether (4-o) was used instead of hexadecylglycidyl ether (4-a), the title compound (6-o) was obtained.

(2) Preparation of an amide derivative (1-o)

In a similar manner to Example 1-(5) except that the compound (6-o) obtained in the above (1) was used instead of the compound (6-a) and the compound (10-j) obtained in Example 10-(1) was used instead of the compound (10-a), the target amide derivative (1-o) was obtained.

The amide derivative (1-o) so obtained has the following physical properties:

White solid. IR(KBr, cm$^{-1}$): 3320, 2930, 2860, 1630, 1550, 1470, 1380, 1260, 1210, 1120, 720. $^1$H-NMR(CDCl$_3$, δ): 0.72–0.99 (m, 9H), 0.99–1.95 (m, 57H), 1.83 (t, J=7.6 Hz, 2H), 2.16 (t, J=7.6 Hz, 2H), 2.39 (t, J=7.6 Hz, 2H), 3.10–3.62 (m, 13H), 3.33 (s, 3H), 3.82–4.02 (m, 1H), 5.35–5.58 (m, 1H).

EXAMPLE 16

Preparation of an amide derivative (1-p) represented by the formula (1) in which R$^5$ represents

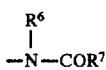

and R$^1$ through R$^7$ represent the following groups, respectively:

R$^1$: C$_{12}$H$_{25}$—
R$^2$: —(CH$_2$)$_3$—
R$^3$: CH$_3$O—
R$^4$: —(CH$_2$)$_{11}$—

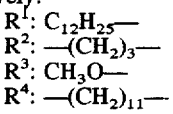

R$^6$: H
R$^7$: CH$_3$(CH$_2$)$_m$CHCH$_3$ (CH$_2$)$_n$— wherein m+n=10–16, m=4–10, n=4–10, and m and n stand for numbers having distribution with m=7 and n=7 as peaks, respectively.

(1) Preparation of N-(3-dodecyloxy-2-hydroxypropyl)-N-3-methoxypropylamine (6-p)

In a similar manner to Example 1-(1) except that dodecylglycidyl ether (4-p) was used instead of hexadecylglycidyl ether (4-a), the title compound (6-p) was obtained.

(2) Preparation of an amide derivative (1-p)

In a similar manner to Example 1-(5) except that the compound (6-p) obtained in the above (1) was used instead of the compound (6-a) and the compound (10-j) obtained in Example 10-(1) was used instead of the compound (10-a), the target amide derivative (1-p) was obtained.

The amide derivative (1-p) so obtained has the following physical properties:

White solid. IR(KBr, cm$^{-1}$): 3330, 2930, 1650, 1560, 1470, 1380, 1260, 1215, 1100, 750. $^1$H-NMR(CDCl$_3$, δ): 0.72–1.00 (m, 9H), 1.00–1.95 (m, 65H), 1.83 (t, J=7.6 Hz, 2H), 2.16 (t, J=7.6 Hz, 2H), 2.38 (t, J=7.6 Hz, 2H), 3.10–3.58 (m, 13H), 3.33 (s, 3H), 3.80–4.00 (m, 1H), 5.35–5.60 (m, 1H).

EXAMPLE 17

Preparation of an amide derivative (1-q) represented by the formula (1) in which R$^5$ represents

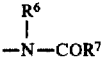

and R$^1$ through R$^7$ represent the following groups, respectively:

R$^1$: C$_{18}$H$_{37}$—
R$^2$: —(CH$_2$)$_3$—
R$^3$: CH$_3$O—
R$^4$: —(CH$_2$)$_{11}$—

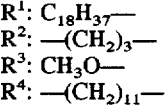

R$^6$: H
R$^7$: CH$_3$(CH$_2$)$_m$CHCH$_3$(CH$_2$)$_n$— wherein m+n=10–16, m=4–10, n=4–10, and m and n stand for numbers having distribution with m=7 and n=7 as peaks, respectively.

(1) Preparation of N-(3-octadecyloxy-2-hydroxypropyl)-N-3-methoxypropylamine (6-q)

In a similar manner to Example 1-(1) except that octadecylglycidyl ether (4-q) was used instead of hexadecylglycidyl ether (4-a), the title compound (6-q) was obtained.

(2) Preparation of an amide derivative (1-q)

In a similar manner to Example 1-(5) except that the compound (6-q) obtained in the above (1) was used instead of the compound (6-a) and the compound (10-j) obtained in Example 10-(1) was used instead of the compound (10-a), the target amide derivative (1-q) was obtained.

The amide derivative (1-q) so obtained has the following physical properties:

White solid. Melting point: 66.5°–69° C. IR(KBr, cm$^{-1}$): 3400, 2930, 2860, 1640, 1550, 1470, 1380, 1260, 1210, 1110, 720. $^1$H-NMR(CDCl$_3$, δ) : 0.72–0.98 (m, 9H) , 1.05–1.80 (m, 77H), 1.81–1.94 (m, 2H), 2.13 (t, J=7.6 Hz, 2H), 2.35 (t, J=7.6 Hz, 2H), 3.15–3.60 (m, 13H), 3.40 (s, 3H), 3.79–4.00 (m, 1H), 5.35–5.52 (m, 1H).

EXAMPLE 18

Preparation of an amide derivative (1-r) represented by the formula (1) in which R$^5$ represents

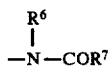

and R$^1$ through R$^7$ represent the following groups, respectively:

R$^1$: CH$_3$(CH$_2$)$_m$CHCH$_3$(CH$_2$)$_n$— wherein m+n=10–16, m=4–10, n=4–10, and m and n stand for numbers having distribution with m=7 and n=7 as peaks, respectively.

R$^2$: —(CH$_2$)$_3$—
R$^3$: CH$_3$O—
R$^4$: —(CH$_2$)$_{11}$—

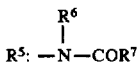

R$^6$: H
R$^7$: CH$_3$(CH$_2$)$_m$CHCH$_3$(CH$_2$)$_n$— wherein m+n=10–16, m=4–10, n=4–10, and m and n stand for numbers having distribution with m=7 and n=7 as peaks, respectively.

(1) Preparation of N-(3-methyl-branched-isostearyloxy-2-hydroxypropyl)-N-3-methoxypropylamine (6-r)

In a similar manner to Example 1-(1) except that methyl-branched isostearylglycidyl ether (4-k) was used instead of hexadecylglycidyl ether (4-a), the title compound (6-r) was obtained.

(2) Preparation of an amide derivative (1-r)

In a similar manner to Example 1-(5) except that the compound (6-r) obtained in the above (1) was used instead of the compound (6-a) and the compound (10-j) obtained in Example 10-(1) was used instead of the compound (10-a), the target amide derivative (1-r) was obtained.

The amide derivative (1-r) so obtained has the following physical properties:

White viscous solid. IR(KBr, cm$^{-1}$): 3320, 2930, 2860, 1640, 1550, 1470, 1380, 1220, 1110, 750. $^1$H-NMR(CDCl$_3$, δ): 0.70–1.00 (m, 12H), 1.02–1.82 (m, 74H), 1.82–1.97 (m, 4H), 2.14 (t, J=7.6 Hz, 2H), 2.34 (t, J=7.6 Hz, 2H), 3.14–3.60 (m, 13H), 3.38 (s, 3H), 3.80–4.00 (m, 1H), 5.34–5.50 (m, 1H).

EXAMPLE 19

Preparation of an amide derivative (1-s) represented by the formula (1) in which R$^5$ represents

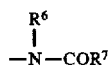

and R$^1$ through R$^7$ represent the following groups, respectively:

R$^1$: C$_{22}$H$_{45}$—
R$^2$: —(CH$_2$)$_3$—
R$^3$: CH$_3$O—
R$^4$: —(CH$_2$)$_{11}$—

R$^6$: H
R$^7$: CH$_3$(CH$_2$)$_m$CHCH$_3$(CH$_2$)$_n$— wherein m+n=10–16, m=4–10, n=4–10, and m and n stand for numbers having distribution with m=7 and n=7 as peaks, respectively.

(1) Preparation of N-(3-docosanoloxy-2-hydroxypropyl)-N-3-methoxypropylamine (6-s)

In a similar manner to Example 1-(1) except that docosanylglycidyl ether (4-s) was used instead of hexadecylglycidyl ether (4-a), the title compound (6-s) was obtained.

(2) Preparation of an amide derivative (1-s)

In a similar manner to Example 1-(5) except that the compound (6-s) obtained in the above (1) was used instead of the compound (6-a) and the compound (10-j) obtained in Example 10-(1) was used instead of the compound (10-a), the target amide derivative (1-s) was obtained.

The amide derivative (1-s) so obtained has the following physical properties:

White solid. Melting point: 69.5°–71.0° C. IR(KBr, cm$^{-1}$): 3400, 2930, 2860, 1640, 1620, 1550, 1470, 1380, 1260, 1210, 1110, 720. $^1$H-NMR(CDCl$_3$, δ): 0.71–1.00 (m, 9H), 1.02–1.80 (m, 85H), 1.81–1.97 (m, 2H), 2.15 (t, J=7.6 Hz, 2H), 2.34 (t, J=7.6 Hz, 2H), 3.14–3.60 (m, 13H), 3.38 (s, 3H), 3.78–4.00 (m, 1H), 5.34–5.52 (m, 1H).

EXAMPLE 20

Preparation of an amide derivative (1-t) represented by the formula (1) in which R$^5$ represents

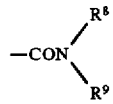

and R$^1$ through R$^5$, R$^8$ and R$^9$ represent the following groups, respectively:

R$^1$: C$_{16}$H$_{33}$—
R$^2$: —(CH$_2$)$_3$—
R$^3$: HO—
R$^4$: —(CH$_2$)$_{10}$—

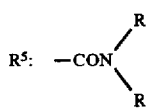

R$^8$: H

-continued

R⁹: C₄H₉CHCH₂—
         |
         C₂H₅

20-(1) Preparation of N-(3-hexadecyloxy-2-hydroxypropyl)-N-2-hydroxyethylamine (6-t).

To a 2-l flask equipped with a stirrer, a dropping funnel, a nitrogen gas inlet tube and a distillation apparatus, 611 g (10.0 mol) of 2-aminoethanol (5-a) and 122 g of ethanol were charged, followed by the dropwise addition of 243 g (0.82 mol) of hexadecyl glycidyl ether (4-a) over 3 hours while stirring under heating to 80° C. in a nitrogen gas atmosphere. After the completion of the dropwise addition, stirring was conducted for further 2 hours at 80° C. From the reaction mixture, ethanol and excessive 2-aminoethanol were distilled off by heating under reduced pressure. The residue was purified by chromatography on a silica gel column, whereby 262 g of the title compound (6-t) were obtained in the form of a white solid (yield: 90% relative to hexadecyl glycidyl ether).

20-(2) Preparation of monomethyl 2-dodecanoate (12-t).

To a 2-l flask equipped with a stirrer and a nitrogen gas inlet tube, 69.1 g (0.3 mol) of 2-dodecanoic acid, 500 ml of methanol and 1.47 g (0.015 mol) of sulfuric acid were charged, followed by stirring under heat at 60° C. in a nitrogen gas atmosphere. The reaction mixture was washed with 1 l of water. The organic layer was dried over anhydrous sodium sulfate and the solvent was distilled off under reduced pressure. The residue was then purified by chromatography on a silica gel column, whereby 36.3 g of the title compound (12-t) were obtained in the form of a white solid (yield: 50% relative to 2-dodecanoic acid).

20-(3) Preparation of methyl 11-(N-(2-ethylhexyl)carbamoylundecanoate (13-t).

To a 500-ml flask equipped with a stirrer and a nitrogen gas inlet tube, 4.40 g (18 mmol) of monomethyl 2-dodecanoate (12-t), 2.33 g (18 mmol) of 2-ethylhexylamine (11-t), 3.04 g (22.5 mmol) of 1-hydroxybenzotriazole, 4.64 g (22.5 mmol) of dicyclohexylcarbodiimide and 150 ml of chloroform were charged, followed by stirring at room temperature for 24 hours. The precipitate so obtained was filtered off and the solvent was distilled off under reduced pressure. The residue was then purified by chromatography on a silica gel column, whereby 5.12 g of the title compound (13-t) were obtained in the form of a white solid (yield: 80% relative to the monomethyl 2-dodecanoate (12-t)).

20-(4) Preparation of an amide derivative (1-t).

To a 50-ml flask equipped with a stirrer and a nitrogen gas inlet tube, 1.72 g (4.8 mmol) of the compound (6-t) obtained in the above (1), 1.42 g (4.0 mmol) of the compound (13-t) obtained in the above (3) and 0.077 g (0.4 mmol) of a 28% solution of sodium methoxide in methanol were charged, followed by stirring under heat at 80° C. and 10 Torr under reduced pressure for 12 hours. The crude product so obtained was purified by chromatography on a silica gel column, whereby 2.92 g of the title compound (1-t) were obtained in the form of a white solid (yield: 80% relative to the compound (13-t)).

The amide derivative (1-t) so obtained has the following physical properties:

White solid. Melting point: 62°–63° C. IR(NaCl, cm⁻¹): 3312, 2932, 2860, 1644, 1556, 1468, 1380, 1234, 1116, 754. ¹H-NMR(CDCl₃, δ) : 0.89 (br t, J=6.4 Hz, 9H), 1.15–1.85 (m, 55H), 2.16 (t, J=7.5 Hz, 2H), 2.40 (t, J=7.5 Hz, 2H), 3.16–4.10 (m, 13H), 5.48 (br, 1H).

EXAMPLE 21

Preparation of an amide derivative (1-u) represented by the formula (1) in which R⁵ represents

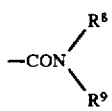

and R¹ through R⁵, R⁸ and R⁹ represent the following groups, respectively:

R¹: C₁₆H₃₃—
R²: —(CH₂)₂—
R³: HO—
R⁴: —(CH₂)₁₀—

R⁵: 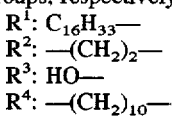

R⁸: HO(CH₂)₂—

R⁹: C₁₆H₃₃OCH₂CHCH₂—
                |
                OH 21-(1) Preparation of dimethyl 2-dodecanoate To a 2-l flask equipped with a stirrer and a nitrogen gas inlet tube, 69.1 g (0.3 mol) of 2-dodecanoic acid, 500 ml of methanol and 1.47 g (0.015 mol) of sulfuric acid were charged, followed by stirring under heat at 60° C. in a nitrogen gas atmosphere for 24 hours. The reaction mixture was washed with 1 l of water. The organic layer was dried over anhydrous sodium sulfate and the solvent was distilled off under reduced pressure. The residue was purified by chromatography on a silica gel column, whereby 25.5 g of the title compound were obtained in the form of a white solid (yield: 33% relative to 2-dodecanoic acid).

21-(2) Preparation of an amide derivative (1-u).

To a 500-ml flask equipped with a stirrer and a nitrogen gas inlet tube, 5.02 g (19.4 mmol) of dimethyl 2-dodecanoate obtained in the above (1), 21.0 g (58.3 mmol) of the compound (6-t) and 0.75 g (3.9 mmol) of a 28% solution of sodium methoxide in methanol were charged, followed by stirring under heat at 80° C. and 10 Torr under reduced pressure for 12 hours. The crude product so obtained was purified by chromatography on a silica gel column, whereby 12.2 g of the title compound (1-u) were obtained in the form of a white solid (yield: 69% relative to dimethyl 2-dodecanoate).

The amide derivative (1-u) so obtained has the following physical properties:

White solid. Melting point: 49°–50° C. IR(NaCl, cm⁻¹): 3396, 2928, 2856, 1624, 1470, 1424, 1366, 1212, 1118, 754. ¹H-NMR(CDCl₃, δ) : 0.88 (t, J=6.3 Hz, 6H), 1.15–1.75 (m, 76H), 2.40 (t, J=7.5 Hz, 4H), 3.23–4.13 (m, 22H).

EXAMPLE 22

Preparation of an amide derivative (1-v) represented by the formula (1) in which R⁵ represents

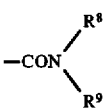

and R¹ through R⁵, R⁸ and R⁹ represent the following groups, respectively:

R¹: C₁₆H₃₃—
R²: —(CH₂)₂—

$R^3$: HO—
$R^4$: —$(CH_2)_{10}$—

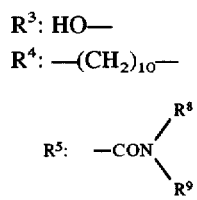

$R^8$: H
$R^9$: $C_5H_{11}$—CH=CH—$CH_2$—CH=CH—$(CH_2)_8$—

22-(1) Preparation of 9,12-octadecadienylamine (11-v).

To a 1-l flask equipped with a stirrer, a dropping funnel and a nitrogen gas inlet tube, 50 ml of tetrahydrofuran and 5.69 g (0.15 mol) of aluminum lithium hydride were charged, followed by the dropwise addition of 14.0 g (0.05 mol) of linoleic acid amide over 30 minutes while stirring at room temperature under a nitrogen gas atmosphere. After the completion of the dropwise addition, stirring was conducted for further 12 hours at 60° C. To the reaction mixture, 16 g (0.05 mol) of sodium sulfate decahydrate were charged, whereby excessive aluminum lithium hydride was decomposed. The solid content in the system was removed by filtration and the solvent was distilled off under reduced pressure. The residue was purified by chromatography on a silica gel column, whereby 9.05 g of the title compound (11-v) were obtained in the form of a white solid (yield: 68% relative to linoleic acid amide).

22-(2) Preparation of methyl 11-(N-(9,12-octadecadienyl)carbamoyl)undecanoate (13-v).

In a similar manner to Example 20-(3), except that the compound (11-v) obtained in the above (1) was used instead of the compound (11-t), the title compound (13-v) was obtained.

22-(3) Preparation of an amide derivative (1-v).

In a similar manner to Example 20-(4), except that the compound (13-v) obtained in the above (2) was used instead of the compound (13-t), the target amide derivative (1-v) was obtained.

The amide derivative (1-v) so obtained has the following physical properties:

White solid. Melting point: 82°–83° C. IR(NaCl, cm$^{-1}$): 3320, 2924, 2852, 1618, 1538, 1464, 1430, 1370, 1262, 1106. $^1$H-NMR(CDCl$_3$, δ): 0.85–0.91 (m, 6H), 1.15–1.70 (m, 62H), 1.99–2.18 (m, 6H), 2.39 (t, J=7.5 Hz, 2H), 2.77 (t, J=5.7 Hz, 2H), 3.18–4.20 (m, 15H), 5.22–5.44 (m, 5H).

EXAMPLE 23

Preparation of an amide derivative (1-w) represented by the formula (1) in which $R^5$ represents

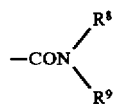

and $R^1$ through $R^5$, $R^8$ and $R^9$ represent the following groups, respectively:

$R^1$: $C_{16}H_{33}$—
$R^2$: —$(CH_2)_2$—
$R^3$: HO—
$R^4$: —$(CH_2)_{10}$—

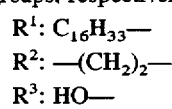

$R^8$: $C_{18}H_{37}$—
$R^9$: $C_{18}H_{37}$—

23-(1) Preparation of methyl 11-(N,N-dioctadecylcarbamoyl)undecanoate (13-w).

In a similar manner to Example 20-(3), except for the use of distearylamine (11-w) instead of the compound (11-t), the title compound (13-w) was obtained.

23-(2) Preparation of an amide derivative (1-w).

In a similar manner to Example 20-(4), except that the compound (13-w) obtained in the above (2) was used instead of the compound (13-t), the target amide derivative (1-w) was obtained.

The amide derivative (1-w) so obtained has the following physical properties:

Colorless oil. IR(NaCl, cm$^{-1}$): 3388, 2928, 2856, 1732, 1644, 1460, 1378, 1304, 1110, 862, 752, 720. $^1$H-NMR (CDCl$_3$, δ): 0.88 (t, J=6.1 Hz, 9H), 1.10–2.00 (m, 108H), 2.22 (t, J=7.6 Hz, 2H), 2.39 (t, J=7.5 Hz, 2H), 3.15–4.20 (m, 17H).

EXAMPLE 24

Preparation of an amide derivative (1-x) represented by the formula (1) in which $R^5$ represents

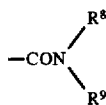

and $R^1$ through $R^5$, $R^8$ and $R^9$ represent the following groups, respectively:

$R^1$: $C_{16}H_{33}$—
$R^2$: —$(CH_2)_2$—
$R^3$: $CH_3O$—
$R^4$: —$(CH_2)_{10}$—

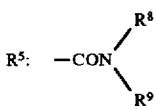

$R^8$: H
$R^9$: $C_5H_{11}$—CH=CH—$CH_2$—CH=CH—$(CH_2)_8$—

24-(1) Preparation of N-(3-hexadecyloxy-2-hydroxypropyl)-N-(2-methoxyethyl)amine (6-x).

In a similar manner to Example 20-(1), except for the use of 2-methoxyethylamine instead of 2-aminoethanol, the title compound (6-x) was obtained.

24-(2) Preparation of an amide derivative (1-x).

In a similar manner to Example 22-(3), except that the compound (13-x) obtained in the above (1) was used instead of the compound (13-v), the target amide derivative (1-x) was obtained.

The amide derivative (1-x) so obtained has the following physical properties:

White solid. Melting point: 57°–59° C. IR(NaCl, cm$^{-1}$): 3324, 2920, 2854, 1620, 1540, 1458, 1426, 1366, 1264, 1102. $^1$H-NMR(CDCl$_3$, δ): 0.86–0.89 (m, 6H), 1.10–1.70 (m, 62H), 2.00–2.18 (m, 6H), 2.39 (t, J=7.5 Hz, 2H), 2.77 (t, J=5.7 HZ, 2H), 3.18–4.24 (m, 17H), 5.26–5.42 (m, 5H).

EXAMPLE 25

Preparation of an amide derivative (1-y) represented by the formula (1) in which $R^5$ represents

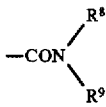

and $R^1$ through $R^5$, $R^8$ and $R^9$ represent the following groups, respectively:

$R^1$: $C_{16}H_{33}$—
$R^2$: —$(CH_2)_2$—
$R^3$: $CH_3O$—
$R^4$: —$(CH_2)_{10}$—

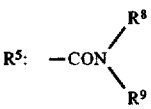

$R^8$: H

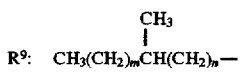

wherein m+n=11–16, m=4–10, n=5–11, and m and n stand for numbers having distribution with m=7 and n=8 as peaks, respectively.

25-(1) Preparation of N-(3-hexadecyloxy-2-hydroxypropyl)-N-(3-methoxypropyl)amine (6-y).

In a similar manner to Example 20-(1), except for the use of 3-methoxypropylamine instead of 2-aminoethanol, the title compound (6-y) was obtained.

25-(2) Preparation of isostearylamine (11-y).

In a similar manner to Example 22-(1), except for the use of isostearic acid amide instead of linoleic acid amide, the title compound (11-y) was obtained.

25-(3) Preparation of methyl 11-(N-isostearylcarbamoyl)undecanoate (13-y).

In a similar manner to Example 13-(3), except that the compound (11-y) obtained in the above (2) was used instead of the compound (11-t), the title compound (13-y) was obtained.

25-(4) Preparation of an amide derivative (1-Y).

In a similar manner to Example 20-(4), except that the compound (6-y) obtained in the above (1) was used instead of the compound (6-t) and the compound (13-y) obtained in the above (3) was used instead of the compound (13-t), the target amide derivative (1-y) was obtained.

The amide derivative (1-y) so obtained has the following physical properties:

White solid. Melting point: 61°–64° C. IR(NaCl, cm$^{-1}$): 3416, 3328, 2924, 2854, 1644, 1616, 1548, 1470, 1378, 1214, 1112, 952, 722 $^1$H-NMR(CDCl$_3$, δ): 0.82–0.91 (m, 9H), 1.05–1.76 (m, 74H), 1.83 (m, 2H), 2.15 (t, J=7.6 Hz, 2H), 2.37 (t, J=7.5 Hz, 2H), 3.18–3.59 (m, 16H), 3.90 (m, 1H), 5.41 (br, 1H).

EXAMPLE 26

Preparation of an amide derivative (1-z) represented by the formula (1) in which $R^5$ represents

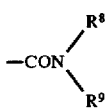

and $R^1$ through $R^5$, $R^8$ and $R^9$ represent the following groups, respectively:

$R^1$: $C_{16}H_{33}$—
$R^2$: —$(CH_2)_2$—
$R^3$: $HO(CH_2)_2O$—
$R^4$: —$(CH_2)_{10}$—

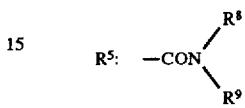

$R^8$: H
$R^9$: $C_5H_{11}$—CH=CH—CH$_2$—CH=CH—$(CH_2)_8$—

26-(1) Preparation of N-(3-hexadecyloxy-2-hydroxypropyl)-N-(2-(2-hydroxyethoxy)ethyl)amine (6-z).

In a similar manner to Example 20-(1), except for the use of 2-(2-aminoethoxy)ethanol instead of 2-aminoethanol, the title compound (6-z) was obtained.

26-(2) Preparation of an amide derivative (1-z).

In a similar manner to Example 22-(3), except that the compound (6-z) obtained in the above (1) was used instead of the compound (6-t), the target amide derivative (1-z) was obtained.

The amide derivative (1-z) so obtained has the following physical properties:

White solid. Melting point: 78°–79° C. IR(NaCl, cm$^{-1}$): 3322, 2926, 2854, 1620, 1540, 1468, 1434, 1368, 1264, 1104. $^1$H-NMR(CDCl$_3$, δ): 0.85–0.89 (m, 6H), 1.15–1.80 (m, 62H), 2.00–2.18 (m, 6H), 2.38 (t, J=7.5 Hz, 2H), 2.77 (t, J=5.7 Hz, 2H), 3.18–4.15 (m, 19H), 5.28–5.46 (m, 5H).

EXAMPLE 27

Preparation of an amide derivative (1-a) represented by the formula (1) in which $R^5$ represents

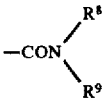

and $R^1$ through $R^5$, $R^8$ and $R^9$ represent the following groups, respectively:

$R^1$: $C_{16}H_{33}$—
$R^2$: —$(CH_2)_2$—
$R^3$: H
$R^4$: —$(CH_2)_8$—

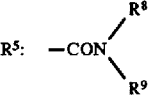

$R^8+R^9$: —$(CH_2)_2O(CH_2)_2$—

27-(1) Preparation of N-(3-hexadecyloxy-2-hydroxypropyl)-N-ethylamine (6-α).

To a 2-l flask equipped with a stirrer, a dropping funnel, a nitrogen gas inlet tube and a distillation apparatus, 500 ml (about 6 mol) of a 70% aqueous ethylamine solution were charged, followed by the dropwise addition of a solution of 119 g (0.4 mol) of hexadecyl glycidyl ether dissolved in 500 ml of ethanol over one hour while stirring at room temperature under a nitrogen gas atmosphere. After the completion of the dropwise addition, stirring was conducted for further 5 hours at room temperature. From the reaction mixture, ethanol, water and excess ethylamine were distilled off by heating under reduced pressure. The residue was purified by chromatography on a silica gel column, whereby 133 g of the title compound (6-α) were obtained in the form of a white solid (yield: 96% relative to hexadecyl glycidyl ether).

27-(2) Preparation of methyl 11-(4-morpholinecarbonyl) undecanoate (13-α).

In a similar manner to Example 20-(3), except for the use of morpholine (11-α) instead of the compound (11-t), the title compound (13-α) was obtained.

27-(3) Preparation of an amide derivative (1-α).

In a similar manner to Example 20-(4), except that the compound (13-') obtained in the above (2) was used instead of the compound (13-t), the target amide derivative (1-α) was obtained.

The amide derivative (1-α) so obtained has the following physical properties:

Colorless oil. IR(NaCl, cm$^{-1}$): 2924, 2854, 1620, 1540, 1470, 1384, 1224, 1120, 768. $^1$H-NMR(CDCl$_3$, δ): 0.88 (t, J=6.3 Hz, 6H), 1.07–1.75 (m, 47H), 2.28–2.41 (m, J=7.5 Hz, 4H), 3.29–4.10 (m, 18H).

EXAMPLE 28

Preparation of an amide derivative (1-β) represented by the formula (1) in which $R^5$ represents —O—$R^{10}$—$R^{11}$ and $R^1$ through $R^5$, $R^{10}$ and $R^{11}$ represent the following groups, respectively:

$R^1$: $C_{16}H_{33}$—
$R^2$: —(CH$_2$)$_3$—
$R^3$: CH$_3$O—
$R^4$: —(CH$_2$)$_{15}$—
$R^5$: —O—$R^{10}$—$R^{11}$
$R^{10}$: single bond
$R^{11}$: H 28-(1) Preparation of N-(3-hexadecyloxy-2-hydroxypropyl)-N-3-methoxypropylamine (6-β).

To a 2-l flask equipped with a stirrer, a dropping funnel, a nitrogen gas inlet tube and a distillation apparatus, 743.2 g (8.34 mol) of 3-methoxypropylamine and 150 ml of ethanol were charged, followed by the dropwise addition of 165.9 g (0.56 mol) of hexadecyl glycidyl ether over 3 hours while stirring under heating to 80° C. in a nitrogen gas atmosphere. After the completion of the dropwise addition, stirring was conducted for further 2 hours at 80° C. From the reaction mixture, ethanol, water and excess 3-methoxypropylamine were distilled off by heating under reduced pressure. The residue was then purified by chromatography on a silica gel column, whereby 196.5 g of the title compound (6-β) were obtained in the form of a white solid (yield: 91% relative to hexadecyl glycidyl ether).

28-(2) Preparation of an amide derivative (1-β).

To a 100-ml flask equipped with a stirrer, a dropping funnel and a distillation apparatus, 11.6 g (30 mmol) of the compound (6-β) obtained in the above (1) and 9.0 g (33 mmol) of methyl 16-hydroxyhexadecanoate (14-β) were charged, followed by the dropwise addition of 0.58 g (3 mmol) of a 28% solution of sodium methoxide in methanol while stirring at 80° C. under a nitrogen gas atmosphere. After the completion of the dropwise addition, the resulting mixture was stirred at 80° C. for one hour. The stirring was conducted for further 10 hours at 80° C. under reduced pressure (10 Torr), whereby the reaction was completed. After cooling, the reaction mixture was purified by chromatography on a silica gel column, whereby 15.7 g of the target amide derivative (1-β) were obtained (yield: 83%).

The amide derivative (1-β) so obtained has the following physical properties:

White solid. Melting point: 64°–66° C. IR(KBr, cm$^{-1}$): 3370, 3320, 2900, 1625, 1470, 1120, 1060, 720. $^1$H-NMR (CDCl$_3$, δ): 0.88 (t, J=8.8 Hz, 3H), 0.95–2.00 (m, 56H), 2.30–2.50 (m, 2H), 3.25–4.20 (m, 14H), 3.33 (s, 3H).

EXAMPLE 29

Preparation of an amide derivative (1-γ) represented by the formula (1) in which $R^5$ represents —O—$R^{10}$—$R^{11}$ and $R^1$ through $R^5$, $R^{10}$ and $R^{11}$ represent the following groups, respectively:

$R^1$: $C_{16}H_{33}$—
$R^2$: —(CH$_2$)$_3$—
$R^3$: CH$_3$O—
$R^4$: —(CH$_2$)$_{15}$—
$R^5$: —O—$R^{10}$—$R^{11}$
$R^{10}$: —CH$_2$—

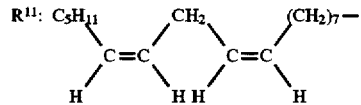

29-(1) Preparation of methyl 16-(9Z, 12Z-octadecadienyloxy)hexadecanoate (14-γ).

To a four-necked 300-l flask equipped with a stirrer, a dropping funnel, a thermometer and a reflux condenser, 2.72 g (10 mmol) of 16-hydroxyhexadecanoic acid, 50 ml of anhydrous tetrahydrofuran, 5 ml of anhydrous hexamethylphosphoryltriamide and 0.24 g (10 mmol) of sodium hydride were charged, followed by stirring at room temperature for 30 minutes in a nitrogen gas stream. The reaction mixture was cooled to −70° C., followed by the addition of 6.25 ml (10 mmol) of a 1.6N solution of butyllithium in hexane. The resulting mixture was then heated to room temperature over 30 minutes, to which 0.24 g (10 mmol) of sodium hydride was added, followed by stirring at room temperature for further 30 minutes. To the reaction mixture, 9.25 g (22 mmol) of 9Z, 12Z-octadecadienyl p-toluenesulfonate (17-γ) were added dropwise and they were stirred under heat at 65° C. for 18 hours. To the reaction mixture so obtained, 150 ml of anhydrous methanol were added, followed by stirring at 65° C. for one hour. After the reaction mixture was cooled down to room temperature, excess alkali was neutralized with an aqueous solution of ammonium chloride. The reaction mixture was extracted with toluene. The solvent was distilled off under reduced pressure. The residue was then purified by flash column chromatography, whereby 0.72 g of the title compound (14-γ) was obtained (yield: 13.5%).

29-(2) Preparation of an amide derivative(1-γ).

In a similar manner to Example 28-(2), except that the compound (14-γ) obtained in the above (1) was used instead of the compound (14-β), the target amide derivative (1-γ) was obtained.

White solid. Melting point: 51°–52° C. IR(KBr, cm$^{-1}$): 3300, 2910, 2850, 1615, 1465, 1100, 720. $^1$H-NMR(CDCl$_3$, δ): 0.80–0.95 (m, 6H), 0.95–1.95 (m, 74H) 1.95–2.15 (m, 4H), 2.25–2.50 (m, 2H), 2.65–2.90 (m, 2H), 3.33 (s, 3H), 3.20–4.25 (m, 16H), 5.20–5.45 (m, 4H).

EXAMPLE 30

Preparation of an amide derivative (1-δ) represented by the formula (1) in which $R^5$ represents —O—$R^{10}$—$R^{11}$ and $R^1$ through $R^5$, $R^{10}$ and $R^{11}$ represent the following groups, respectively:

R¹: C₁₆H₃₃—
R²: —(CH₂)₃—
R³: HO—(CH₂)₂—
R⁴: —(CH₂)₁₅—
R⁵: —O—R¹⁰—R¹¹

R¹⁰: $-\overset{\overset{O}{\|}}{C}-$

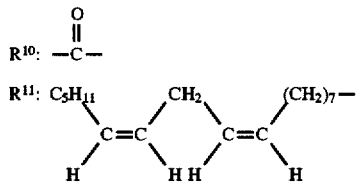

R¹¹: C₅H₁₁—C=C—CH₂—C=C—(CH₂)₇—
         |   |   |    |   |
         H   H   H    H   H 30-(1) Preparation of N-(3-hexadecyloxy-2-hydroxypropyl)-N-(2-(2-hydroxyethoxy)ethylamine (6-δ).

IR(KBr, cm⁻¹): 3315, 2925, 2855, 1615, 1465, 1440, 1215, 1110, 720. ¹H-NMR(CDCl₃, δ): 0.80–1.00 (m, 6H), 1.00–1.75 (m, 70H), 1.95–2.50 (m, 8H), 2.65–2.80 (m, 2H), 3.20–4.35 (m, 17H), 4.05 (t, J=6.6 Hz, 2H), 5.25–5.50 (m, 4H).

EXAMPLE 31

Preparation of an amide derivative (I-ε) represented by the formula (1) in which R⁵ represents —O—R¹⁰—R¹¹ and R¹ through R⁵, R¹⁰ and R¹¹ represent the following groups, respectively:

R¹: C₁₆H₃₃—
R²: —(CH₂)₃—
R³: CH₃O—
R⁴: —(CH₂)₁₅—
R⁵: —O—R¹⁰—R¹¹

R¹⁰: $-\overset{\overset{O}{\|}}{C}-$

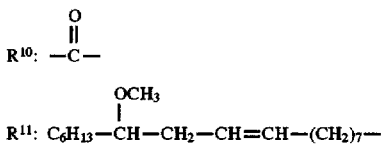

R¹¹: C₆H₁₃—CH—CH₂—CH=CH—(CH₂)₇—
              |
              OCH₃

31-(1) Preparation of 12-methoxy-9-octadecenoic acid

To a 1-l flask equipped with a stirrer, a dropping funnel and a condenser, 24 g (0.6 mol) of 60% sodium hydride and 500 ml of dimethylformamide were charged, followed by the dropwise addition of a solution of 163.3 g (0.5 mol) of ethyl ricinoleate in 142 g (1.0 mol) of methyl iodide over one hour while stirring at 40° C. under a nitrogen gas atmosphere. After In a similar manner to Example 28-(1), except for the use of 2-(2-aminoethoxy)ethanol instead of 3-methoxypropylamine, the title compound (6-δ) was obtained.

30-(2) Preparation of methyl 16-(9Z, 12Z-octadecadienoyloxy)hexadecanoate (14-δ).

To a 300-ml flask equipped with a stirrer, a dropping funnel and a thermometer, 4.30 g (15 mmol) of methyl 16-hydroxyhexadecanoate, 8.41 g (13 mmol) of linoleic acid, 7.87 g (30 mmol) of triphenylphosphine and 100 ml of tetrahydrofuran were charged, followed by the dropwise addition of 5.22 g (30 mmol) of diethyl azodicarboxylate over one hour while stirring at room temperature. After the completion of the dropwise addition, stirring was conducted for further 4 hours at room temperature. The solvent was distilled off under reduced pressure. The residue was purified by flash chromatography on silica gel, whereby 6.76 g of the title compound (14-δ) were obtained (yield: 82%).

30-(3) Preparation of an amide derivative (1-δ).

In a similar manner to Example 28-(2), except that the compound (6-δ) obtained in the above (1) was used instead of the compound (6-β) and the compound (14-δ) obtained in the above (2) was used instead of the compound (14-β), the target amide derivative (1-δ) was obtained.

White solid. Melting point: 48°–49° C. the completion of the dropwise addition, stirring was conducted for further 6 hours at 40° C. To the reaction mixture so obtained, hexane was added, followed by washing with an aqueous solution of ammonium chloride and an aqueous solution of sodium thiosulfate and then concentration under reduced pressure. The residue was then purified by chromatography on a silica gel column, whereby 155.8 g of ethyl 12-methoxy-9-octadecenoate were obtained (yield: 92%).

To a 1-l flask equipped with a stirrer, 68.1 g (0.2 mol) of the above-obtained ethyl 12-methoxy-9-octadecenoate, 600 ml of ethanol and 45 g of a 50% aqueous solution of potassium hydroxide were charged, followed by stirring at 50° C. for 4 hours. To the reaction mixture so obtained, hexane was added. The resulting mixture was neutralized with 3N hydrochloric acid, followed by washing with saturated saline. After concentration under reduced pressure, the residue was purified by chromatography on a silica gel column, whereby 58.3 g of the title compound were obtained (yield: 93%).

31-(2) Preparation of methyl 16-(12-methoxy-9-octadecenoyloxy)hexadecanoate

In a similar manner to Example 30-(2), except that the compound obtained in the above (1) was used instead of linoleic acid, the title compound was obtained.

31-(3) Preparation of an amide derivative (1-ε).

In a similar manner to Example 28-(2), except that the compound obtained in the above (2) was used instead of the compound (14-β), the target amide derivative (1-ε) was obtained.

White solid. Melting point: 48°–50° C. IR(KBr, cm⁻¹): 3310, 2900, 2870, 1610, 1550, 1465, 1105, 720. ¹H-NMR (CDCl₃, δ): 0.88 (br t, J=6.4 Hz, 6H), 1.10–1.95 (m, 76H), 1.95–2.10 (m, 2H), 2.10–2.55 (m, 6H), 3.10–3.70 (m, 12H), 3.33 (s, 3H), 3.34 (s, 3H), 3.80–4.05 (m, 1H), 4.05 (t, J=6.6 Hz, 2H), 5.30–5.60 (2H).

EXAMPLE 32

Preparation of an amide derivative (1-') represented by the formula (1) in which R⁵ represents —O—R¹⁰—R¹¹ and R¹ through R⁵, R¹⁰ and R¹¹ represent the following groups, respectively:

R¹: C₁₆H₃₃—
R²: —(CH₂)₃—
R³: CH₃O—
R⁴: —(CH₂)₁₅
R⁵: —O—R¹⁰—R¹¹

R¹⁰: $-\overset{\overset{O}{\|}}{C}-$

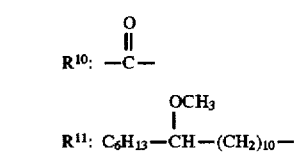

R¹¹: C₆H₁₃—CH—(CH₂)₁₀—
              |
              OCH₃

To a 1-l flask equipped with a stirrer and a hydrogen gas inlet tube, 10.2 g (11.3 mmol) of the compound (1-ε) prepared in Example 4, 1.5 g of 5% palladium carbon and 300 ml of ethanol were charged, followed by stirring at room temperature for 26 hours under a hydrogen gas atmosphere.

The reaction mixture so obtained was filtered and the filtrate was concentrated under reduced pressure. The residue was purified by chromatography on a silica gel column, whereby 9.3 g of the target amide derivative (1-') were obtained (yield: 95%).

White solid. Melting point: 52°–53° C. IR(KBr, cm$^{-1}$): 3330, 2930, 1625, 1550, 1210, 1110, 720. $^1$H-NMR(CDCl$_3$, δ): 0.88 (br t, J=6.4 Hz), 1.10–1.95 (m, 84H), 2.29 (t, J=7.5 Hz, 2H), 7.39 (t, J=7.5 Hz, 2H), 3.00–3.70 (m, 12H), 3.32 (s, 3H), 3.33 (s, 3H), 3.80–4.00 (m, 1H), 4.05 (t, J=6.6 Hz, 2H).

EXAMPLE 33

Preparation of an amide derivative (1-aa) represented by the formula (1) in which R$^5$ represents —O—R$^{10}$—R$^{11}$ and R$^1$ through R$^5$, R$^{10}$ and R$^{11}$ represent the following groups, respectively:

R$^1$: C$_{16}$H$_{33}$—
R$^2$: —(CH$_2$)$_3$—
R$^3$: CH$_3$O—
R$^4$: —(CH$_2$)$_{15}$—
R$^5$: —O—R$^{10}$—R$^{11}$

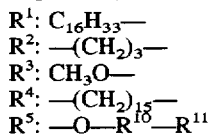

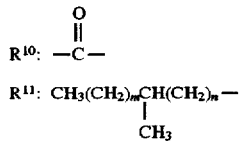

wherein m+n=10–16, m=4–10, n=4–10, and m and n stand for numbers which have distribution with m=7 and n=7 as peaks, respectively.

33-(1) Preparation of methyl (methyl-branched isostearoylyloxy)hexadecanoate

In a similar manner to Example 30-(2), except for the use of methyl-branched isostearic acid instead of linoleic acid, the title compound was obtained.

33-(2) Preparation of an amide derivative (1-aa).

In a similar manner to Example 28-(2), except that the compound obtained in the above (1) was used instead of the compound (14-β), the target amide derivative (1-aa) was obtained.

White solid. Melting point: 55°–57° C. IR(KBr cm$^{-1}$): 3335, 2930, 1630, 1550, 1465, 1110, 720. $^1$H-NMR(CDCl$_3$, δ): 0.75–1.00 (m, 9H), 1.00–1.95 (m, 83H), 2.29 (t, J=7.5 Hz, 2H), 2.40 (t, J=7.5 Hz, 2H), 3.15–4.00 (m, 12H), 3.33 (s, 3H), 4.05 (t, J=6.6 Hz, 2H).

EXAMPLE 34

Preparation of an amide derivative (1-ab) represented by the formula (1) in which R$^5$ represents —O—R$^{10}$—R$^{11}$ and R$^1$ through R$^5$, R$^{10}$ and R$^{11}$ represent the following groups, respectively:

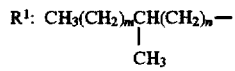

wherein m+n=10–16, m=4–10, n=4–10, and m and n stand for numbers having distribution with m=7 and n=7 as peaks, respectively.

R$^2$: —(CH$_2$)$_2$—
R$^3$: H
R$^4$: —(CH$_2$)$_{15}$—

R$^5$: —O—R$^{10}$—R$^{11}$

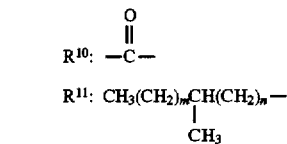

wherein m+n=10–16, m=4–10, n=4–10, and m and n stand for numbers having distribution with m=7 and n=7 as peaks, respectively.

34-(1) Preparation of N-(3-methyl-branched isostearyloxy-2-hydroxypropyl)-N-ethylamine In a similar manner to Example 28-(1), except that ethylamine was used instead of 3-methoxypropylamine and methyl-branched isostearyl glycidyl ether was used instead of hexadecyl glycidyl ether, the title compound was obtained.

34-(2) Preparation of an amide derivative (1-ab).

In a similar manner to Example 28 (1), except that the compound obtained in the above (1) was used instead of the compound (6-β) and the compound obtained in Example 33 (1) was used instead of the compound (14-β), the target amide derivative (1-ab) was obtained.

White solid. Melting point: 54°–57° C. IR(KBr, cm$^1$): 3380, 2930, 1625, 1550, 1470, 1380, 1210, 1100, 720. $^1$H-NMR(CDCl$_3$, δ): 0.75–1.00 (m, 12H), 1.00–1.85 (m, 85H), 2.29 (t, J=7.5 Hz, 2H), 2.40 (t, J=7.5 Hz), 3.15–4.00 (m, 10H), 4.05 (t, J=6.6 Hz, 2H).

Compared with the compound represented by the formula (2) proposed in Japanese Patent Laid-Open No. 30695/1990, and the compound represented by the formula (3) proposed in Japanese Patent Laid-Open No. 70030/1995, the amide derivatives of the present invention described in the above examples have lower melting points, for excellent solubility and stability to base ingredients. When incorporated in an external composition, the amide derivatives of the present invention are excellent in ease of compositioning and in stability of the compositions.

Test 1

Compositions according to the present invention for topical application to human skin were produced, comprising 10% of the amide derivative of the present invention shown below in Table 1, and 90% of squalane. The percutaneous water transpiration amount and the percutaneous absorption amount of the compositions were measured by the testing method described below. For comparison, a control composition of only squalane was similarly measured. The results are shown in Table 1.

Test Procedure

Male Wister rats were raised using only feed free of essential fatty acids. Those rats showing symptoms of essential fatty acid deficiency were used for the test. After the back of each rat suffering from the essential fatty acid deficiency was shaved thoroughly, the composition for evaluation was applied to the shaved part once a day for three weeks. A group consisting of five rats was tested for each composition. After three weeks, tests were conducted for percutaneous water transpiration amount and percutaneous absorption amount, as described below.

Percutaneous Water Transpiration Amount

After the back of each rat was washed with warm water and the rat was allowed to stand for one hour (at room temperature of 23° C. and humidity of 45%), water transpiration amount from the skin was measured by an evaporimeter. The percutaneous water transpiration amount of rats having a normal barrier function was generally 10 or lower, while that of rats suffering from essential fatty acid deficiency was as high as 20–30, or higher. Such an increase in the percutaneous water transpiration amount is considered to be caused by a lowering in the barrier function of the stratum corneum. In other words, the higher the percutaneous water transpiration amount is, the lower the barrier function of the stratum corneum, and the skin becomes rough. It is therefore possible to study the effect of the invention product as a composition for topical application to human skin by measuring the value of the percutaneous water transpiration amount. Measured values shown in Table 1 are averages.

Percutaneous Absorption Amount

After the back of the rat was washed with warm water (37° C.), the dorsal skin was cut off and fixed on a percutaneous absorption chamber with the epidermis side up. The lower receiver was filled with a phosphate buffer solution. Onto the epidermis, 1 ml of a phosphate buffer solution containing $^{14}$C-salicylic acid of 37 KBq was added, which was then allowed to stand. Two hours later, 1 ml of the phosphate buffer solution was drawn from the lower receiver and the radioactive amount of the $^{14}$C-salicylic acid penetrated into the solution was measured, whereby the percutaneous absorption was evaluated. In the case of a normal rat having normally-maintained barrier function, $C^{14}$-salicylic acid hardly penetrated into the skin, while in the case of a rat which suffered from an essential-fatty-acid deficiency disease and was disordered in the barrier function, a significant increase in the penetration amount of $^{14}$C-salicylic acid was observed. Measured values shown in Table 1 are averages.

TABLE 1

| Amide derivative | Percutaneous water transpiration amount | Percutaneous absorption amount |
|---|---|---|
| Invention Product | | |
| Compound of Example 1 | 11.3 | 542 |
| Compound of Example 2 | 10.8 | 560 |
| Compound of Example 3 | 13.7 | 1017 |
| Compound of Example 4 | 16.0 | 1429 |
| Compound of Example 5 | 21.9 | 1996 |
| Compound of Example 6 | 11.2 | 651 |
| Compound of Example 7 | 23.0 | 1685 |
| Compound of Example 8 | 17.8 | 1372 |
| Compound of Example 9 | 12.5 | 643 |
| Compound of Example 10 | 11.2 | 489 |
| Compound of Example 11 | 22.0 | 1613 |
| Compound of Example 12 | 17.1 | 1032 |
| Compound of Example 13 | 27.6 | 2027 |
| Compound of Example 14 | 18.5 | 1467 |
| Compound of Example 15 | 11.0 | 541 |
| Compound of Example 16 | 14.3 | 1152 |
| Compound of Example 17 | 12.1 | 719 |
| Compound of Example 18 | 17.6 | 1298 |

TABLE 1-continued

| Amide derivative | Percutaneous water transpiration amount | Percutaneous absorption amount |
|---|---|---|
| Compound of Example 19 | 16.4 | 1012 |
| Compound of Example 20 | 24.1 | 1372 |
| Compound of Example 21 | 21.9 | 847 |
| Compound of Example 22 | 10.4 | 631 |
| Compound of Example 23 | 18.9 | 512 |
| Compound of Example 24 | 11.5 | 539 |
| Compound of Example 25 | 10.8 | 732 |
| Compound of Example 26 | 9.4 | 622 |
| Compound of Example 27 | 17.1 | 1434 |
| Compound of Example 28 | 18.6 | 873 |
| Compound of Example 29 | 20.3 | 1511 |
| Compound of Example 30 | 12.8 | 714 |
| Compound of Example 31 | 13.6 | 1117 |
| Compound of Example 32 | 15.4 | 1343 |
| Compound of Example 33 | 12.1 | 685 |
| Compound of Example 34 | 22.9 | 1785 |
| Comparative Product | | |
| Composition composed only of squalane | 29.3 | 2954 |

As is apparent from the results shown in Table 1, the invention products containing the amide derivative of the present invention each show excellent suppression of percutaneous water transpiration and percutaneous absorption, compared with the comparative product composed of squalane only.

This application is based on Japanese Patent Applications 229875/1995, 258511/1995 and 019762/1996, filed with the Japanese Patent Office on Sep. 7, 1995, Oct. 5, 1995 and Feb. 6, 1996, respectively, the entire contents of which applications are incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A compound of formula (1):

wherein:

$R^1$ represents a linear or branched $C_{1-40}$ hydrocarbon group;

$R^2$ represents a linear or branched $C_{1-6}$ alkylene group;

$R^3$ represents a hydrogen atom, a hydroxyl group, or a linear or branched $C_{1-12}$ alkoxyl group which may be substituted by one or more hydroxyl groups;

$R^4$ represents a linear or branched divalent $C_{1-39}$ hydrocarbon group; and $R^5$ represents

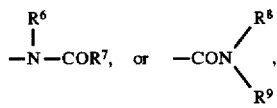

wherein:

$R^6$ represents a hydrogen atom or a $C_{1-6}$ hydrocarbon group, $R^7$ represents a linear, branched, or cyclic $C_{1-40}$ hydrocarbon group which may contain one or more oxygen atoms, $R^8$ and $R^9$ are the same or different, and are individually a hydrogen atom or a linear, branched, or cyclic $C_{1-40}$ hydrocarbon group containing an oxygen atom, or are coupled together to form a divalent $C_{1-40}$ hydrocarbon group which may contain one or more oxygen atoms, $R^{10}$ represents a carbonyl group, a methylene group, or a single bond, and $R^{11}$ represents a linear, branched, or cyclic $C_{1-40}$ hydrocarbon group which may contain one or more oxygen atoms, with the proviso that when $R^{10}$ represents a single bond, $R^{11}$ represents a hydrogen atom, and with the proviso that when $R^5$ represents

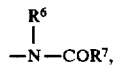

$R^3$ does not represent a hydroxyl group.

2. The compound of claim 1, wherein:

$R^1$ represents a linear or branched $C_{1-26}$ hydrocarbon group;

$R^4$ represents a linear, saturated divalent $C_{5-31}$ hydrocarbon group, $R^7$ represents a linear, branched, or cyclic $C_{7-25}$ hydrocarbon group which may contain one or more hydroxyl groups, ether groups, carbonyl groups, carboxyl groups, or carboxylate groups;

$R^8$ and $R^9$ are the same or different and are individually a hydrogen atom or a linear, branched, or cyclic $C_{7-25}$ hydrocarbon group which may contain one or more hydroxyl groups, ether groups, carbonyl groups, carboxyl groups, or carboxylate groups, or $R^8$ and $R^9$ are coupled together to form a $C_{1-40}$ alkylene, alkenylene, alkylene-O-alkylene, or alkenylene-O-alkenylene; and $R^{11}$ represents a linear, branched, or cyclic $C_{7-25}$ hydrocarbon group which may contain one or more hydroxyl groups, ether groups, carbonyl groups, carboxyl groups, or carboxylate groups.

3. The compound of claim 1, wherein $R^5$ is:

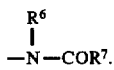

4. The compound of claim 3, wherein $R^7$ is:

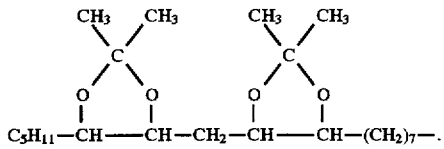

5. The compound of claim 3, wherein $R^7$ is:

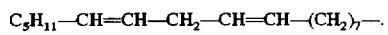

6. The compound of claim 3, wherein $R^7$ is:

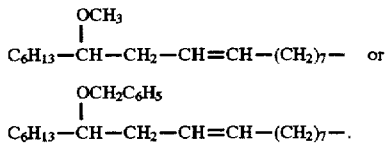

7. The compound of claim 3, wherein $R^7$ is:

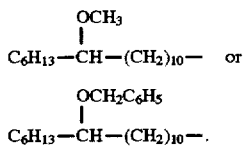

8. The compound of claim 3, wherein $R^7$ is:

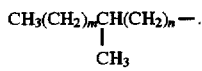

9. The compound of claim 3, wherein $R^7$ is $C_{17}H_{35}$.

10. The compound of claim 1, wherein $R^5$ is:

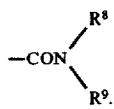

11. The compound of claim 10, wherein $R^9$ is:

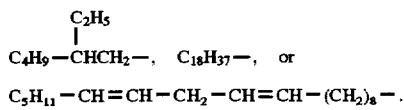

12. The compound of claim 10, wherein $R^9$ is:

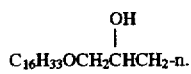

13. The compound of claim 10, wherein $R^8$ and $R^9$ together represent $-(CH_2)_2O(CH_2)_2$.

14. A composition for topical application to human skin, comprising the compound of claim 1 and a dermatologically acceptable carrier.

15. A method of treating skin disorders, comprising applying a dermatologically effective amount of the compound of claim 1 to the skin of a subject in need thereof.

16. A compound of formula (1):

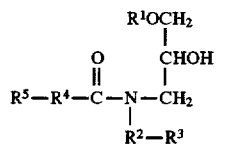

wherein:

$R^1$ represents a linear or branched $C_{1-40}$ hydrocarbon group;

$R^2$ represents a linear or branched $C_{1-6}$ alkylene group;

$R^3$ represents a hydrogen atom, or a linear or branched $C_{1-12}$ alkoxyl group which may be substituted by one or more hydroxyl groups;

$R^4$ represents a linear or branched divalent $C_{1-39}$ hydrocarbon group; and $R^5$ represents —O—$R^{10}$—$R^{11}$, wherein:

$R^6$ represents a hydrogen atom or a $C_{1-6}$ hydrocarbon group, $R^7$ represents a linear, branched, or cyclic $C_{1-40}$ hydrocarbon group which may contain one or more oxygen atoms, $R^8$ and $R^9$ are the same or different, and are individually a hydrogen atom or a linear, branched, or cyclic $C_{1-40}$ hydrocarbon group containing an oxygen atom, or are coupled together to form a divalent $C_{1-40}$ hydrocarbon group which may contain one or more oxygen atoms, $R^{10}$ represents a carbonyl group or a methylene group, and $R^{11}$ is:

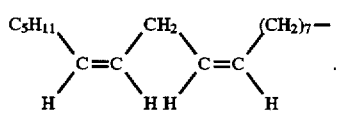

17. A compound of formula (1):

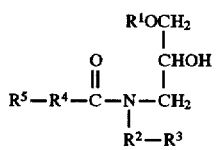

wherein:

$R^1$ represents a linear or branched $C_{1-40}$ hydrocarbon group;

$R^2$ represents a linear or branched $C_{1-6}$ alkylene group;

$R^3$ represents a hydrogen atom, or a linear or branched $C_{1-12}$ alkoxyl group which may be substituted by one or more hydroxyl groups;

$R^4$ represents a linear or branched divalent $C_{1-39}$ hydrocarbon group; and $R^5$ represents —O—$R^{10}$—$R^{11}$, wherein:

$R^6$ represents a hydrogen atom or a $C_{1-6}$ hydrocarbon group, $R^7$ represents a linear, branched, or cyclic $C_{1-40}$ hydrocarbon group which may contain one or more oxygen atoms, $R^8$ and $R^9$ are the same or different, and are individually a hydrogen atom or a linear, branched, or cyclic $C_{1-40}$ hydrocarbon group containing an oxygen atom, or are coupled together to form a divalent $C_{1-40}$ hydrocarbon group which may contain one or more oxygen atoms, $R^{10}$ represents a carbonyl group or a methylene group, and $R^{11}$ is:

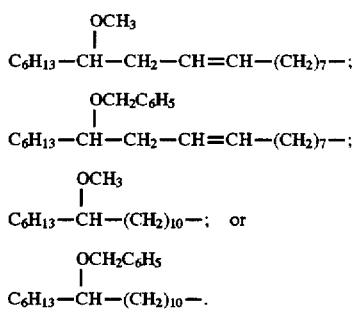

18. A composition for topical application to human skin, comprising the compound of claim 16 and a dermatologically acceptable carrier.

19. A method of treating skin disorders, comprising applying a dermatologically effective amount of the compound of claim 16 to the skin of a subject in need thereof.

20. A composition for topical application to human skin, comprising the compound of claim 22 and a dermatologically acceptable carrier.

21. A method of treating skin disorders, comprising applying a dermatologically effective amount of the compound of claim 17 to the skin of a subject in need thereof.

* * * * *

UNITED STATES PATENT AND TRADEMARK OFFICE
CERTIFICATE OF CORRECTION

PATENT NO. : 5,753,707
DATED : MAY 19, 1998
INVENTOR(S) : Masahide HOSHINO, et al It is certified that error appears in the above-identified patent and that said Letters Patent is hereby corrected as shown below:

Column 46, line 46 ,"claim 22" should read--claim 17--.

Signed and Sealed this

First Day of September, 1998

Attest:

BRUCE LEHMAN

Attesting Officer

Commissioner of Patents and Trademarks